(12) United States Patent
Batinic-Haberle et al.

(10) Patent No.: US 7,485,721 B2
(45) Date of Patent: Feb. 3, 2009

(54) SUBSTITUTED PORPHYRINS

(75) Inventors: Ines Batinic-Haberle, Durham, NC (US); Ivan Spasojevic, Durham, NC (US); Irwin Fridovich, Durham, NC (US)

(73) Assignee: Duke University, Durham, NC (US)

( * ) Notice: Subject to any disclaimer, the term of this patent is extended or adjusted under 35 U.S.C. 154(b) by 175 days.

(21) Appl. No.: 10/456,956

(22) Filed: Jun. 9, 2003

(65) Prior Publication Data

US 2004/0058902 A1    Mar. 25, 2004

Related U.S. Application Data

(60) Provisional application No. 60/386,454, filed on Jun. 7, 2002.

(51) Int. Cl.
C07B 47/00 (2006.01)
C07D 487/22 (2006.01)

(52) U.S. Cl. .................................................. 540/145

(58) Field of Classification Search ................ 514/410, 514/185; 424/9.1, 9.362, 9.61; 540/145; 534/15

See application file for complete search history.

(56) References Cited

U.S. PATENT DOCUMENTS

| | | |
|---|---|---|
| 2,951,799 A | 9/1960 | Sharp |
| 4,614,723 A | 9/1986 | Schmidt |
| 4,657,902 A | 4/1987 | Kappas et al. |
| 4,746,735 A | 5/1988 | Kruper, Jr. et al. |
| 4,758,422 A | 7/1988 | Quay |
| 4,829,984 A | 5/1989 | Gordon |
| 4,837,221 A | 6/1989 | Bonnett |
| 4,851,403 A | 7/1989 | Picker et al. |
| 4,866,054 A | 9/1989 | Dori et al. |
| 4,885,114 A | 12/1989 | Gordon et al. |
| 4,892,941 A | 1/1990 | Dolphin et al. |
| 4,895,719 A | 1/1990 | Radhakrishnam |
| 4,963,367 A | 10/1990 | Ecanow |
| 5,010,073 A | 4/1991 | Kappas et al. |
| 5,051,337 A | 9/1991 | Sakoda et al. |
| 5,087,438 A | 2/1992 | Gordon |
| 5,109,016 A | 4/1992 | Dixon et al. |
| 5,130,245 A | 7/1992 | Marklund et al. |
| 5,162,519 A | 11/1992 | Bonnett |
| 5,169,630 A | 12/1992 | Okaya et al. |
| 5,171,680 A | 12/1992 | Mullenbach et al. |
| 5,192,757 A | 3/1993 | Johnson et al. |
| 5,192,788 A | 3/1993 | Dixon et al. |
| 5,202,317 A | 4/1993 | Bruice |
| 5,217,966 A | 6/1993 | Bruice |
| 5,223,538 A | 6/1993 | Fridovich |
| 5,227,405 A | 7/1993 | Fridovich |
| 5,236,914 A | 8/1993 | Meunier |
| 5,236,915 A | 8/1993 | Fiel |
| 5,248,603 A | 9/1993 | Marklund et al. |
| 5,262,532 A | 11/1993 | Tweedle et al. |
| 5,277,908 A | 1/1994 | Beckman et al. |
| 5,281,616 A | 1/1994 | Dixon et al. |
| 5,284,647 A | 2/1994 | Niedballa |
| 5,366,729 A | 11/1994 | Marklund et al. |
| 5,403,834 A | 4/1995 | Malfroy-Camine et al. |
| 5,405,369 A | 4/1995 | Selman et al. |
| 5,472,691 A | 12/1995 | Marklund et al. |
| 5,493,017 A | 2/1996 | Thieren et al. |
| 5,563,132 A | 10/1996 | Bodaness |

(Continued)

FOREIGN PATENT DOCUMENTS

EP    0 127 797    12/1984

(Continued)

OTHER PUBLICATIONS

Batinic-Haberle et al, "Manganese(III) meso-tetrakis(ortho-N-alkylpyridyl)porphyrins. Synthesis, characterization, and catalysis of $O_2^{\cdot -}$ dismutation", J. Chem. Soc. Dalton Trans., pp. 2689-2696 (2002).

(Continued)

*Primary Examiner*—James O. Wilson
*Assistant Examiner*—Paul V. Ward
(74) *Attorney, Agent, or Firm*—Townsend and Townsend and Crew

(57) ABSTRACT

A series of ortho isomers of meso tetrakis N-alkylpyridylporphyrins (alkyl being methyl, ethyl, n-propyl, n-butyl, n-hexyl, and n-octyl) and their Mn(III) complexes were synthesized and characterized by elemental analysis, uv/vis spectroscopy, electrospray ionization mass spectrometry and electrochemistry. An increase in the number of carbon atoms in the alkyl chains from 1 to 8 is accompanied by an increase in: (a) lipophilicity measured by the chromatographic retention factor, $R_f$; (b) metal-entered redox potential, $E_{1/2}$ from +220 to +367 mV vs NHE, and (c) proton dissociation constant, $pK_{a2}$ from 10.9 to 13.2. A linear correlation was found between $E_{1/2}$ and $R_f$ of the Mn(III) porphyrins and between the $pK_{a2}$ and $R_f$ of the metal-free compounds. As the porphyrins become increasingly more lipophilic, the decrease in hydration disfavors the separation of charges, while enhancing the electron-withdrawing effect of the positively charged pyridyl nitrogen atoms. Consequently, the $E_{1/2}$ increases linearly with the increase in $pK_{a2}$, a trend in porphyrin basicity opposite from the one we previously reported for other water-soluble Mn(III) porphyrins. All of these Mn(III) porphyrins are potent catalysts for superoxide dismutation (disproportionation). Despite the favorable increase of $E_{1/2}$ with the increase in chain length, the catalytic rate constant decreases from methyl (log $k_{cat}$=7.79) to n-butyl, and then increases such that the n-octyl is as potent an SOD mimic as are the methyl and ethyl compounds. The observed behavior originates from an interplay of hydration and steric effects that modulate electronic effects.

6 Claims, 9 Drawing Sheets

U.S. PATENT DOCUMENTS

| | | | |
|---|---|---|---|
| 5,599,924 | A | 2/1997 | Therien et al. |
| 5,604,199 | A | 2/1997 | Funanage |
| 5,610,293 | A | 3/1997 | Riley et al. |
| 5,637,578 | A | 6/1997 | Riley et al. |
| 5,674,467 | A | 10/1997 | Maier et al. |
| 5,747,026 | A | 5/1998 | Crapo |
| 5,767,272 | A | 6/1998 | Wijesekera et al. |
| 5,834,509 | A | 11/1998 | Malfroy-Camine et al. |
| 5,874,421 | A | 2/1999 | Riley et al. |
| 5,948,771 | A | 9/1999 | Danziger |
| 5,976,498 | A | 11/1999 | Neumann et al. |
| 5,976,551 | A | 11/1999 | Mottez et al. |
| 5,994,339 | A | 11/1999 | Crapo et al. |
| 5,994,410 | A | 11/1999 | Chiang et al. |
| 6,013,241 | A | 1/2000 | Marchal et al. |
| 6,046,188 | A | 4/2000 | Malfroy-Camine et al. |
| 6,060,467 | A | 5/2000 | Buelow et al. |
| 6,084,093 | A | 7/2000 | Riley et al. |
| 6,087,493 | A | 7/2000 | Wheelhouse et al. |
| 6,103,714 | A | 8/2000 | Fridovich et al. |
| 6,127,356 | A | 10/2000 | Crapo et al. |
| 6,180,620 | B1 | 1/2001 | Salvemini |
| 6,204,259 | B1 | 3/2001 | Riley et al. |
| 6,214,817 | B1 | 4/2001 | Riley et al. |
| 6,245,758 | B1 | 6/2001 | Stern et al. |
| 6,372,727 | B1 | 4/2002 | Crow et al. |
| 6,395,725 | B1 | 5/2002 | Salvemini |
| 6,403,788 | B1 | 6/2002 | Meunier et al. |
| 6,417,182 | B1 | 7/2002 | Abrams et al. |
| 6,548,045 | B2 | 4/2003 | Sakata et al. |
| 6,566,517 | B2 | 5/2003 | Miura et al. |
| 6,573,258 | B2 * | 6/2003 | Bommer et al. ............. 514/185 |
| 6,602,998 | B2 | 8/2003 | Kobuke et al. |
| 6,624,187 | B1 | 9/2003 | Pandey et al. |
| 2002/0042407 | A1 * | 4/2002 | Fridovich et al. ........... 514/185 |
| 2002/0058643 | A1 | 5/2002 | Cherian et al. |

FOREIGN PATENT DOCUMENTS

| | | | |
|---|---|---|---|
| EP | 0 186 962 | | 7/1986 |
| EP | 0 282 899 | | 9/1988 |
| EP | 0 284 645 | | 10/1988 |
| EP | 0 336 879 | | 10/1989 |
| EP | 0 337 601 | | 10/1989 |
| EP | 0 345 171 | | 12/1989 |
| EP | 0 414 915 | A1 | 3/1991 |
| EP | 0 462 836 | | 12/1991 |
| EP | 0 524 161 | A1 | 1/1993 |
| EP | 0 532 327 | | 3/1993 |
| FR | 2 676 738 | | 11/1992 |
| JP | 02289844 | A2 * | 11/1989 |
| JP | 03273082 | | 12/1991 |
| WO | WO 91/04315 | | 4/1991 |
| WO | WO 91/19977 | | 12/1991 |
| WO | 92/07935 | | 5/1992 |
| WO | WO 92/08482 | | 5/1992 |
| WO | WO 92/15099 | | 9/1992 |
| WO | WO 93/02090 | | 2/1993 |
| WO | WO 94/04614 | | 3/1994 |
| WO | WO 94/05285 | | 3/1994 |
| WO | WO 95/10185 | | 4/1995 |
| WO | WO 95/31197 | | 11/1995 |
| WO | WO 96/09038 | | 3/1996 |
| WO | WO 96/09053 | | 3/1996 |
| WO | WO 96/40148 | | 12/1996 |
| WO | WO 96/40223 | | 12/1996 |
| WO | WO 97/06824 | | 2/1997 |
| WO | WO 97/06830 | | 2/1997 |
| WO | WO 97/06831 | | 2/1997 |
| WO | WO 97/33588 | | 9/1997 |
| WO | WO 97/33877 | | 9/1997 |
| WO | WO 98/33503 | | 6/1998 |
| WO | WO 98/58636 | | 12/1998 |
| WO | WO 99/23097 | | 5/1999 |
| WO | WO 99/55388 | | 11/1999 |
| WO | WO 00/04868 | | 2/2000 |
| WO | WO 00/19993 | | 4/2000 |
| WO | WO 00/23568 | | 4/2000 |
| WO | WO 00/43395 | | 7/2000 |
| WO | WO 00/72893 | | 12/2000 |
| WO | WO 00/75144 | | 12/2000 |
| WO | WO 01/26655 | | 4/2001 |
| WO | WO 01/96345 | | 12/2001 |

OTHER PUBLICATIONS

O'hara et al, "Potentiation of radiation-induced cell kill by synthetic metalloporphyrins", Int. J. Radiat. Oncol. Biol. Phys. 16(4):1049-1052 (1989).

Lee et al, "Rapid decomposition of peroxynitrite by manganese porphyrin-antioxidant redox couples", Bioorganic & Medical Chemistry Letters 7(22):2913-2918 (1997).

Madakyan et al, "New watersoluble metal complexes of meso-tetrakis[3-N-(2'-hydroxy ethyl)pyridyl]porphyrins and their pharmacological activity", Arm. Khim. Zh. 42(11):724-728—Chemical Abstracts 113:653—Abstract No. 114027h, (1975).

Wheelhouse et al, "Cationic Porphyrins as Telomerase Inhibitors; the Interaction of Tetra-(N-methyl-4-pyridyl)porphine with Quadruplex DNA", J. Am. Chem. Soc. 120(13):3261-3262 (1998).

Zahedi, "Semiempirical molecular orbital calculations of biliverdin: study of dynamics and energetics of the self-association of a two-electron oxidation product", Theochem. 531:79-88 (2000).

Lord, "Redox characteristics of nickel and palladium complexes of the open-chain tetrapyrrole octaethylbilindione: a biliverdin model", Inorg. Chem. 39(6):1128-1134 (2000).

Balch, "Isolation and characterization of an iron biliverdin-type complex that is formed along with verdohemochrome during the coupled oxidation of iron (II) octaethylporphyrin", Am. Chem. Soc. 115(20):9056-9061 (1993).

Koerner, "Carbon monoxide production during the oxygenation of cobalt complexes of linear etrapyrroles", Inorg. Chem. 37(5):982-988 (1998).

Balch, "Solid-state self-association of the two-electron oxidation product of a biliverdin analogue", J. Chem. Soc. Chem. Commun. 6:643-644 (1995).

Balch, "Geometric and electronic structure and dioxygen sensitivity of the copper complex of octaethylbilindione, a biliverdin analog", J. Am. Chem. Soc. 115(25):12206-12207 (1993).

Falk, "Contributions to the chemistry of pyrrolic pigments", Tetrahedron 37(4):761-767 (1981).

Burke, "Photochemical and thermal transformations of phytochrome", Chem. Physiol. Bile Pigm., Int. Symp., pp. 509-517 (1975).

Madakyan et al, "Some metal complexes of meso-tetrakis (3-N-substituted pyridyl) porphyrins and their bioactivity", Arm. Khim. Zh. 42(10):642-646 (1989).

Crapo et al, 721195, Document No. 123:218443 (1995).

Sheldon, Chapter 1 in Metalloporphyrins in Catalytic Oxidations, Marcel Dekker, Inc. (1994).

Butje et al, "Electronic Spectra, Resonance Raman Spectra and Solution Properties of Water-soluble (Cu(II), Ni(II) and Co(III) Porphyrins", Inorg. Chim. Acta 167:97-108 (1990).

Davila et al, "Sterically-Hindered Zinc Porphyrins for Solar-Energy Conversion", J. Chem. Soc., Chem. Commun., pp. 525-527 (1987).

Kaufmann et al, "Separation of the Rotational Isomers of Tetrakis(N-methyl-2-pyridiniumyl)porphyrin and Crystal Sturcture of $\alpha,\alpha,\alpha,\beta$-(Tetrakis(N-methyl-2-pyridiniumyl)porphyrin)copper Hexacyanoferrate", Inorg. Chem. 34:5073-5079 (1995).

Sari et al, "Interaction of Cationic Porphyrins with DNA: Importance of the Number and Position of the Charges and Minimum Structural Requirements for Intercalation", Biochemistry 29:4205-4215 (1990).

Vodzinskii et al, "Porphyrines and Their Derivatives. XX. Synthesis and Properties of 2-Nitro-5,10,15,20-tetraheterylporphyrins", Russian Journal of Organic Chemistry 34(6):882-885 (1998).

Hambright et al, "Manganese(III) porphyrin isomers: polarography and stannous ion reduction kinetics", Porphyrin Chem. Adv., editor: Longo, [Pap. Porphyrin Symp.], pp. 284-292, Meeting Date 1977.

Batinic-Haberle et al, "A Potent Superoxide Dismutase Mimic" Manganese[B]-Octabromo-meso-tetrakis-(N-methylpyridinium-4-yl)Porphyrin, Archives of Biochemistry and Biophysics 343(2):225-233 (1997).

Crapo and Tierney, "Superoxide dismutase and pulmonary oxygen toxicity", Am. J. Physiol. 226:1401-1407 (1974).

Tjahjono et al, "Cationic porphyrins bearing diazolium rings: synthesis and their interaction with calf thymus DNA", Biochemica et Biophisica Acta 1472:333-343 (1999).

Callot and Schaeffer, "Ring contraction of homoporphyrins to porphyrins, *meso*-Reactivity of 5,10,15-Triphenylporphin and Porphin", J. Chem. Research (S):51 (1978).

Inoue et al, "Expression of a Hybrid Cu/Zn-type Superoxide . . . ," J. Bio. Chem., vol. 266, No. 25, pp. 16409-16414 (1991).

Day et al, "Manganic Porphyrins Possess Catalase Activity . . . ," Arch. Biochem. Biophys., vol. 347, No. 2, pp. 256-262 (1997).

Tsan, M-F., "Superoxide Dismutase and Pulmonary Oxygen Toxicity," XP-002074505, pp. 286-290, (2001).

Foran et al, "Effect of Electrolyte Concentration on Axial Anion Ligation in Manganese(III) *meso*-Tetraphenylporphyrin Chlorides", Inorg. Chem. 31:1463-1470 (1992).

Milgrom, Facile Aerial Oxidation of a Porphyrin. Part 3. Some Metal Complexes of *meso*-Tetrakis-(3,5-di-t-butyl-4-hydroxyphenyl)porphyrin, J. Chem. Soc. Perkin Trans. 11:71-79 (1988).

Bockhorst and Hoehn-Berlage, "An Optimized Synthesis of Manganese *meso*-Tetra(4-sulfonato-phenyl)porphine: A Tumor-Selective MRI Contrast Agent", Tetrahedron 50(29):8657-8660 (1994).

Keinan et al, "Catalytic Antibodies. Circular Dichroism and UV-Vis Studies of Antibody-Metalloporphyrin Interactions", Inorg. Chem. 31:5433-5438 (1992).

Marx, "Role of Gene Defect in Heredity ALS Clarified", Science 261:986 (1993).

Epp et al, "Superoxide Dismutase Activity of Manganese Chelates", 76-78 (1986).

Bors et al, "An expanded function for superoxide dismutase", Chemical Abstracts 115:388 (1991), Abstract No. 109185h.

Milgrom et al, "Redox Behaviour of Phenolic Porphyrins in Basic Solutions: A Reappraisal", Free Rad. Res. 24(1):19-29 (1996).

Szabo et al, "Evaluation of the relative contribution of nitric oxide and peroxynitrite to the suppression of mitochondrial respiration in immunostimulated macrophages using a manganese mesoporphyrin superoxide dismutase mimetic and peroxynitrite scavenger", FEBS Letters 381:82-86 (1996).

Patel et al, "Requirement for Superoxide in Excitotoxic Cell Death", Neuron 16:345-355 (1996).

Bamford et al, "The Squalestatins: Synthesis and Biological Activity of Some C3-Modified Analogues: Replacement of a Carboxylic Acid or Methyl Ester with an Isoelectric Heterocyclic Functionality", J. Med. Chem. 38:3502-3513 (1995).

Szabo et al, "Peroxynitrite Is Involved in the Pathogenesis of the Vascular Contractile and Energetic Failure in Endotoxic Shock", Shock Society Meeting (1996).

Stralin et al, "Effects of Oxidative Stress on Expression of Extracellular Superoxide Dismutase, CuZn-Superoxide Fibroblast", Biochem. J. 298:347-352 (1994).

Folz et al, "Extracellular Superoxide Dismutase (SOD3): Tissue-Specific Expression, Genomic Characterization, and Computer-Assisted Sequence Analysis of the Human EC SOD Gene", Genomics 22:162-171 (1994).

Clyde et al, "Distribution of Manganese Superoxide Dismutase mRNA in Normal and Hyperoxic Rat Lung", American Journal of Respiratory Cell and Molecular Biology 8:530-537 (1993).

Wolberg et al, Electrocical and Electron Paramagnetic Resonance Studies of Metalloporphyrins and Their Electrochemical Oxidation Products:, Journal of the American Chemical Society 92(10):2982-2990 (1970).

Pasternack et al, "Superoxide Dismutase Activities of an Iron Porphyrin and Other Iron Complexes", Journal of the American Chemical Society 101(4):1026-1031 (1979).

Winkelman, James, "The Distribution of Tetraphenylporphinesulfonate in the Tumor-bearing Rat", Cancer Research 22:589-596 (1962).

Moisy et al; "Catalytic Oxidation of 2,6-Di-*Ter*butylphenol by Molecular Oxygen Electroassisted by Poly(Pyrrole-Manganese-Porphyrin)", New J. Chem. 13:511-514 (1989).

Malinski et al, "Characterization of Conductive Polymeric Nickel(II) Tetrakis(3-methoxy-4-hydroxy-phenyl)Porphyrin as an Anodic Material for Electrocatalysis", J. Electrochem. Soc. 138(7):2008-2015 (1991).

Weinraub et al, "Chemical properties of water-soluble porphyrins. 5. Reactions of some manganese (III) porphyrins with the superoxide and other reducing radicals", Int. J. Radiat. Biol. 50(4):649-658 (1986) (Abs).

Fajer et al, "η-Cation Radicals and Dications of Metalloporphyrins", Journal of the American Chemical Society 92(11):3451-3459 (1970).

Pasternack et al, "Aggregation of Nickel(II), Coppwer (II), and Zinc(II) Derivatives of Water-Soluble Porphyrins", Inorganic Chemistry 12(11):2606-2610 (1973).

Datta-Gupta et al, "Synthetic Porphyrins. I. Synthesis and Spectra of Some *para*-Substituted *meso*-Tetraphenylporphines (1)", J. Heterocycl. Chem. 3:495-502 (1996).

Harriman et al, "Photochemistry of Manganese Porphyrins Part 2.-Photoreduction", pp. 1543-1552, 1997.

Longo et al, "The Synthesis and Som e Physical Properties of *ms*-Tetra(pentafluorophenyl)-porphin and *ms*-Tetraphenylporphines (1)", Notes 6:927-931 (1969).

Barnitz-McLaughlin et al, "Reactions of $Fe^{III}$(*meso*-α,α,α,α-tetrakis[0-[N-methylisonicotinamido)phenyl]porphyrin)$^{5+}$ and $Fe^{III}$(*meso*-tetrakis[N-methylpyridinium-4-yl]porphyrin)$^{5+}$ with $NC^-$, $CO_2^-$, and $O_2^-$ ", Inorg. Chem. 32:941-947 (1993).

Pasternack et al, "On the Aggregation of Meso-Substituted Water-Soluble Porphyrins", Journal of American Chemical Society 94(13):4511-4517 (1972).

Datta-Gupta et al, "Synthetic Porphyrins II Preparation and Spectra of Some Metal Chelates of *para*", Journal of Substituted-*mesa*-Tetraphenylporphines, J. of Pharmaceutical Science 57(2):300-304 (1968).

Boissinot et al, "Rational Design and Expression of a Heparin-Targeted Human Superoxide Dismutase", Biochemical and Biophysical Research Communication 190(1):250-256 (1993).

Oury et al, "Cold-induced Brain Edema in Mice", The Journal of Biological Chemistry 268(21):15394-15398 (1993).

Oury et al, "Extracellular superoxide dismutase, nitric oxide, and central nervous system $O_2$ toxicity", Proc. Natl. Acad. Sci. USA 89:9715-9719 (1992).

Pasternack et al, "Catalyst of the Disproportionation of Superoxide by Metalloporphyrins III", Journal of Inorganic Biochemistry 15:261-267 (1981).

Oury et al, "Establishment of Transgenic Mice Expressing Human Extracellular Superoxide Dismutase", American Review of Respiratory Disease 143(4):A515 (1991), International Conference Supplement Abstracts—No. 236.

Oury et al, "Transgenic Mice Superexpressing Human Extracellular Superoxide Dismutase Show Increased Resistance to Cold-induced Brain Edema, But are More Susceptible to Hyperbaric Oxygen", American Review of Respiratory Disease 145(4):A713 (1992), International Conference Supplement Abstracts—No. 211.

Oury et al, "Immunocytochemical Localization of Extracellular Superoxide Dismutase in Human Lung", American Revew of Respiratory Disease 147(4):A713 (1993), International Conference Supplement Abstracts—No. 246.

Oury, Tim D., "Extracellular Superoxide Dismutase and Nitric Oxide: Transgenic and Immunocytochemical Studies", Dissertation submitted in partial fulfillment of the requirements for the degree of Doctor of Philosophy in the Department of Pathology in the Graduate School of Duke University (Jun. 17, 1993).

Gosh, "Substituent Effects on Valence Ionization Potentials of Free Base Porphyrins: Local Density Functional Calculations and Their Relevance to Electrochemical and Photoelectron Spectroscopic Studies", J. Am. Chem. Soc. 117:4691-4699 (1995).

De Peretti et al, "Imidazol[2,1-b]benzoxazole-3-acetamide derivatives, their preparation, and their therapeutic use", Chemical Abstracts 121:1016, Abstract No. 121:200896u, 1966.

Oberley et al, "Anticancer activity of metal compounds with superoxide dismutase activity", Agents and Actions 15(5/6):535-538 (1984).

Collman et al, "Synthesis of "Face to Face" Porphyrin Dimers Linked by 5,15-Substituents: Potential Binuclear Multielectron Redox Catalysts", J. Am. Chem. Soc. 103:516-533 (1981).

Gassman et al, "Electronic Effects of Peripheral Substituents in Porphyrins: X-ray Photoelectron Spectroscopy and ab Initio Self-Consistent Field Calculations", J. Am. Chem. Soc. 114:9990-10000 (1992).

Bishop et al, "The Reaction of Thiomides with Phosphorus Ylides", J. Org. Chem. 56:5079-5091 (1991).

Picker et al, "Cobalt(III) complexes of water soluble synthetic meso-substituted porphyrins as radiation sensitizers for oxic and hypoxic tumor cells", 8-Radiation 112:405 (1990) Abstract No. 112:73026d.

McCord et al, "Superoxide Dismutase-An Enzymic Function for Erythrocuprein", Biochemistry 492, p. 346, 1969.

McCord et al, Superoxide Dismutase An Enzymic Function for Erythrocuprein (Hemocuprein), The Journal of Biological Chemistry 244(22):6049-6055 (1969).

Crapo et al, "Superoxide Dismutase and Oxygen Toxicity", Clinical Research, p. 222, 1995.

Crapo et al, "The Failure of Aerosolized Superoxide Dismutase to Modify Pulmonary Oxygen Toxicity", American Review of Respiratory Disease 115:1027-1033 (1977).

Joester et al, "Superoxide Dismutase Activity of $Cu^{2+}$-Amino Acid Chelates", FEBS Letters 25(1):25-28 (1972).

Brigelius et al, "Superoxide Dismutase Activity of Low Molecular Weight Cu2+-Chelates Studied by Pulse Radiolysis", FEBS Letters 47(1):72-75 (1974).

Sorenson, John R.J., "Copper Chelates as Possible Active Forms of the Antiarthritic Agents", Journal of Medicinal Chemistry 19(1):135-148 (1976).

deAlvare et al, "Mechanism of Superoxide Anion Scavenging Reaction by Bis-(Salicylato)-Copper(II) Complex", Biochemical and Biophysical Research Communications 69(3):687-694 (1976).

Halliwell, Barry, "The Superoxide Dismutase Activity of Iron Complexes", FEBS Letters 56(1):34-38 (1975).

McClune et al, "Catalysis of Superoxide Dismutation by Iron-Ethylenediaminetetraacetic Acid Complexes. Mechanism of the Reaction and Evidence for the Direct Formation of an Iron(III)-Ethylenediaminetetraacetic Acid Peroxo Complex from the Reaction of Superoxide with Iron(II)-Ethylenediaminetetraacetic Acid", Communications to the Editor, p. 5220-5222 (1977).

Diguiseppi et al, "Putative Superoxide Dismutase Activity of Iron-EDTA: A Reexamination", Archives of Biochemistry and Biophysics 203(1):145-150 (1980).

Robertson, Jr. Et al, "Does Copper-D-Penicillamine Catalyze the Dismutation of $O_2^-$?", Archives of Biochemistry and Biophysics 203(2):830-831 (1980).

Werringloer et al, "The Integration of Divalent Copper and the Microsomal Electron Transport System", The Journal of Biological Chemistry, 254(23):11839-11846 (1979).

Pasternack et al, "Catalyst of the Disproportionation of Superoxide by Metalloporphyrins", Journal of Inorganic Biochemistry 11:261-267 (1979).

Archibald et al, Manganese and Defenses against Oxygen Toxicity in *Lactobacillus plantarum*, Journal of Bacteriology 145(1):442-451 (1981).

Archibald et al, Manganese, Superoxide Dismutase, Oxygen Tolerance in Some Lactic Acid Bacteria, Journal of Bacteriology 146(3):928-936 (1981).

Archibald et al, The Scavenging of Superoxide Radical by Manganous Complex: In Vitro, Archives of Biochemistry and Biophysics 214(2):452-463 (1982).

Archibald et al, Investigations of the State of the Manganese in *Lactobacillus plantarum*, Archives of Biochemistry and Biophysics 215(2):589-596 (1982).

Darr et al, "A Mimic of Superoxide Dismutase Activity Based Upon Desferrioxamine B and Manganese(IV)", Archives of Biochemistry and Biophysics 258(2):351-355 (1987).

Beyer, Jr., Characterization of a Superoxide Dismutase Mimic Prepared from Desferrioxamine and $MnO_2$, Archives of Biochemistry and Biophysics 271(1):149-156 (1989).

Faulkner et al, "Characterization of Mn(III) Complexes of Linear and Cyclic Desferrioxamines as Mimics of Superoxide Dismutase Activity", Archives of Biochemistry and Biophysics 310(2):341-346 (1994).

Faulkner et al, Stable Mn(III) Porphyrins Mimic Superoxide Dismutase in Vitro and Substitute for It in Vivo, The Journal of Biological Chemistry 269(38):23471-23476 (1994).

Liochev et al, "A Cationic Manganic Porphyrin Inhibits Uptake of Paraquat by *Escherichia coli*", Archives of Biochemistry and Biophysics 321(1):271-275 (1995).

Peretz et al, "Chemical properties of water-soluble porphyrins 3. The reaction of superoxide radicals with some metalloporphyrins", Int. J. Radiat. Biol. 42(4):449-456 (1982).

Baudry et al, "Salen-Manganese Complexes are Superoxide Dismutase-Mimics", Biochemical and Biophysical Research Communication 192(2):964-968 (1993).

Gonzalez et al, "EUK-8, a Synthetic Superoxide Dismutase and Catalase Mimetic, Ameliorates Acute Lung Injury in Endotexemic Swine", The Journal of Pharmacology and Experimental Therapeutics 275(2):798-806 (1995).

Deune et al, "Prevention of Ischemia-Reperfusion Injury with a Synthetic Metalloprotein Superoxide Dismutase Mimic, SC52608", Plastic and Reconstructive Surgery 98(4):711-718 (1996).

Lowe et al, "Comparison of the cardiovascular effects of two novel superoxide dismutase mimetics, SC-55858 and SC-54417, in conscious dogs", European Journal of Pharmaloty 304:81-86 (1996).

Weiss et al, "Manganese-based Superoxide Dismutase Mimetics Inhjibit Neutral Infiltration in Vivo", The Journal of Biological Chemistry 271(42):26149-26156 (1996).

Jin et al, "A new route to water soluble porphyrins: phosphonium and ammonium type cationic porphyrins and self-assembly", Chem. Commun., pp. 1939-1940 (1996).

Pitié et al, "Oxidation at Carbon-1' of DNA Deoxyriboses by the Mn-TMPyP/KHSO5 System Results from a Cytochrome P-450-Type Hydroxylation Reaction", J. Am. Chem. Soc. 117:2935-2936 (1995).

Libby et al, "Cationic Porphyrin Derivatives As Inhibitors of Polyamine Catabolism", Biochemical Pharmacology 50(9):1527-1530 (1995).

Ilan et al, "Superoxide Dismuting Activity of an Iron Porphyrin", Inorg. Nucl. Chem. Letters 17(3/4):93-96 (1981).

Solomon et al, "Chemical properties of Water-Soluble Porphyrins. 2. The Reaction of Iron(III) Tetrakis(4-N-methylpyridyl)porphyrin with the Superoxide Radical Dioxygen Couple", J. Phys. Chem. 86:1842-1849 (1982).

Weinraub et al, "Chemical Properties of Water-Soluble Porphyrins. 1. Equilibria between Some Ligands and Iron(III) Tetrakis (4-*N*-methylpyridyl)porphyrin", J. Phys. Chem. 86:1839-1842 (1982).

Day et al, "A Metalloporphyrin Superoxide Dismutase Mimetic Protects Against Paraquat-Induced Endothelial Cell Injury, in Vitro", The Journal of Pharmacology and Experimental Therapeutics 275(3):1227-1232 (1995).

Kariya et al, "Superoxide Dismutase (SOD) Activity with Fe-chlorin e6-Na and Suppression of Malignant Tumor Growth in Rats", Cancer Bioteheraphy 10(2):139-145 (1995).

Liochev et al, A Cationic Manganic Porphyrin Inhibits Uptake of Paraquat by *Escherichia coli*, Archives of Biochemistry and Biophysics 321(1):271-275 (1995).

Lindsey et al, "Rothemund and Adler-Longo Reactions Revisited: Synthesis of Tetraphenylphorins under Equilibrium Conditions", J. Org. Chem. 52:827-836 (1987).

Lindsey et al, "$^{252}$Cf Plasma Desorption Mass Spectrometry in the Synthesis of Porphyrin Model Systems", Anal. Chem. 64(22):2804-2814 (1992).

Tsvetkov et al, "Infrared spectra of copper complexes of tetraphenylporphyrin", Izvestiya Vysshikh Uchebnykh Zavedenij, Khimiya I Khimicheskaya Tekhnologiya 27(7)):782-785 (1984)—English Abstract.

Berezin et al, Effect of ligand structure on the kinetic stability of tetraphenylporphyrin complexes of zinc and cadmium, Zhurnal Neorganicheskoi Khimii 25(10):2645-2652 (1980)—English Abstract.

Berezin et al, "Factors determining the stability of complexes of copper with p-substituted derivatives of tetraphenylporphine", Zhurnal Fizicheskoi Khimil 53(11):2716-2719 (1979)—English Abstract.

Wang et al, Structure of LB film of 5,10,15,20-tetra(p-ethoyycarbonphenyl)porphyrin, Yingyong Huaxue 10(2):87-88 (1993)—English Abstract.

Ohkawa et al, "Assay for Lipid Peroxides in Animal Tissues by Thiobarbituric Acid Reaction", Analytical Biochemistry 95:351 (1979).

Yue et al, "Carvedilol, a New Vasodilator and Beta Adrenoceptor Antagonist, is an Antioxidant and Free Radical Scavenger", The Journal of Pharmacology and Experimental Therapeutics 263:(1992).

Song et al, "Anti-HIV activities of anionic metalloporphyrins and related compounds", Antiviral Chemistry and Chemotherapy 8(2):85 (1997).

Harriman and Porter, "Photochemistry of Manganese Porphyrins", J. Chem. Soc. 275:1532-1542 (1979).

Bedioui et al, "Metalloporphyrin-Polypyrrole Film Electrode: Characterization and Catalytic Application", J. Electroanal. Chem. 207:87-99 (1986).

Ruoslahti et al, "Arg-Gly-Asp: A Versatile Cell Recognition Signal", Cell 44:517-518 (1986).

Kumar et al, "Radioprotection by Antioxidant Enzymes and Enzyme Mimetics", Pharmac. Ther. 39:301-309 (1988).

Weiss et al, "Evaluation of Activity of Putative Superoxide Dismutase Mimics", The Journal of Biological Chemistry 2638(31):23049-23054 (1993).

Parge et al, "Atomic structures of wild-type and thermostable mutant recombinant human Cu,Zn superoxide dismutase", Proc. Natl. Acad. Sci. USA 89:6109-6113 (1992).

Lappin, "Part III Bioinorganic Studies", Inorganic Reaction Mechanisms 7:334-343 (1981).

Sharma et al, "Synthesis of amphiphilic 5-(4-N-alkylpyridiniumyl)-10,15,20-triphenylporphyrins and their aggregational properties in different solvent systems", Chemical Abstracts vol. 123, No. 1 (1995)—Abstract No. 9222q.

Schneider et al, "Ligand-Porphyrin Complexes: Quantitative Evaluation of Stacking and Ionic Contributions", J. Org. Chem. 59:7464-7472 (1994).

Giraudeau et al, "Substituent Effects in the Electroreduction of Porphyrins and Metalloporphyrins", Journal of the American Chemical Society 101(14):3857-3862 (1979).

Naruta et al, J. Am. Chem. Soc. 113:3595-3596 (1991).

Leondiadis et al, J. Org. Chem. 54:6135-6138 (1989).

Schlözer et al, "Reactivity of Unsubstituted Porphin", German version: Angew. Chem. 87:388 (1975).

Rosenfeld et al, "Safety and pharmacokinetics of recombinant human superoxide dismutase administered intratracheally to premature neonates with respiratory distress syndrome", Pediatrics 97(Pt 1):811-817 (1996).

Comhair et al, "Rapid loss of superoxide dismutase activity during antigen-induced asthmatic response", Lancet 355(9204):624 (2000).

Lee and Smith, "Syntheses of symmetrically substituted 5-alkyl- and 5-aryl-dihydrodipyrrins and of porphyrins and bisporphyrins therefrom", J. Chem. Soc. Perkin Trans 1:1215-1227 (1997).

Louati et al, "Homophophyrines: Effets D'Une Coupure De Conjugaison Cyclique Sur La Reactivite Redox Des Porphyrines", Nouv. J. Chim. 2:163-168 (1978).

Elangovan and Krishnan, "Photophysical properties of porphyrin amphiphiles bearing pyridinium alkyl groups", Chemical Physics Letters 194(1,2):139-146 (1992).

Hambright, Peter, "An acid solvolysis kinetic study of manganese(II)-tetra(2-N-methylpyridyl)porphine", J. Inorg. Chem. 39:1102-1103 (1977).

Vergeldt et al, "Intramolecular Interactions in the Ground and Excited State of Tetrakis(N-methylpyridyl)porphyrins", J. Phys. Chem. 99:4397-4405 (1995).

Hunt et al, "Amphiphilic peroxynitrite decomposition catalysts in liposomal assemblies", Chemistry & Biology 4(11):845-858 (1997).

Dwyer et al, "Protective Properties of Tin- and Manganese-Centered Porphyrins Against Hydrogen Peroxide-Mediated Injury in Rat Astroglial Cells", J. Neurochem 71:2497 (1998).

Spasojevic and Batinic-Haberle, "Manganese(III) complexes with porphyrins and related compounds as catalytic scavengers of superoxide", Inorganica Chimica Acta 317:230-242 (2001).

Mackensen et al, "Neuroprotection from Delayed Postischemic Administration of a Metalloporphyrin Catalytic Antioxidant", The Journal of Neuroscience 21(13):4582-4592 (2001).

Gauuan et al, "Superoxide dismutase mimetics: synthesis and structure-activity relationship study of MnTBAP analogues", Bioorganic & Medicinal Chemistry 10(9):3013-3021 (2002).

Laehdesmaeki et al, "Detection of Oxygen Consumption of Cultured Adherent Cells by Bead Injection Spectroscopy", Analytical Chemistry 71(22):5248-5252 (1999).

Vinogradov and Wilson, "Palladium catalyzed carbonylation of Br-substituted porphyrins", Tetrahedron Letters 39(49):8935-8938 (1998).

Lindsey et al, "Synthesis of tetraphenylporphyrins under very mild conditions", Tetrahedron Letters 27(41):4969-4970 (1986).

Walker et al, "Models of the cytochromes b. 5. EPR Studies of low-spin iron(III) tetraphenylporphyrins", Journal of the American Chemical Society 106(23):6888-6898 (1984).

Batinic-Haberle et al, "The *Ortho* Effect Makes Manganese(III) *Meso*-Tetrakis-(*N*-Methylpyridinium-2-yl)Porphyrin a Powerful and Potentially Useful Superoxide Dismutase Mimic", The Journal of Biological Chemistry 273(38):24521-24528 (1998).

Yu and Su, "Electrocatalytic reduction of nitric oxide by water-soluble manganese porphyrins", Journal of Electroanalytical Chemistry 368:323-327 (1994).

Hambright et al, "Synthesis and Characterization of New Isomeric Water-Soluble Porphyrins Tetra(2-*N*-methylpyridyl)porphine and Tetra(3-*N*-methylpyridyl)porphine", Inorganic Chemistry 15(9):2314-2315 (1976).

Batinic-Haberle et al, Relationship among Redox Potentials, proton Dissociation Constants of Pyrrolic Nitrogens, and in Vivo and in Vitro Superoxide Dismutation Activities of Manganese(III) and Iron(III) Water-Soluble Porphyrins, Inorg. Chem. 38:4011-4022 (1999).

Batinic-Haberle et al, "Manganese(III) *meso-tetrakis(ortho-N-*alkylpyridyl)porphyrins. Synthesis, characterization, and catalysis of $O_2$ dismutation", J. Chem. Soc., Dalton Trans. pp. 2689-2696 (2002).

Kobayashi et al, "Oxidative Stress Relief for Cancer-Bearing Hosts by the Protein-Bound Polysaccharide of *Coriolus versicolor* QUEL with SOD Mimicking Activity", Cancer Biotherapy 9(1):55-62 (1994).

Richards et al, "Observation of a Stable Water-Soluble Lithium Porphyrin", Inorg. Chem. 35:1940-1944 (1996).

Bloodsworth et al, "Manganese-Porphyrin Reactions with Lipids and Lipoproteins", Free Radical Biology & Medicine 28(7):1017-1029 (2000).

Szabo et al, "Part I: Pathogenetic Role of Peroxynitrite in the Development of Diabetes and Diabetic Vascular Complications: Studies With FP15, A Novel Potent Peroxynitrite Decomposition Catalyst", Molecular Medicine 8(10):571-580 (2002).

Mabley et al, "Part II: Beneficial Effects of the Peroxynitrite Decomposition Catalyst FP15 in Murine Models of Arthritis and Colitis", Molecular Medicine 8(10):581-590 (2002).

Sonis et al, "AEOL 10150, a catalytic antioxidant, reduces the incidence and duration of radiation-induced oral mucositis in a hamster", European Journal of Cancer 37:S361 (2001)—Abstract.

Konorev et al, "Cell-Permeable Superoxide Dismutase and Glutathione Peroxidase Mimetics Afford Superior Protection against Doxorubicin-Induced Cardiotoxicity: The Role of Reactive Oxygen and Nitrogen Intermediates", Archives of Biochemistry and Biophysics 368(2):421-428 (1999).

Beil et al., "*Helicobacter pylori* Reduces Intracellular Glutathione in Gastric Epithelial Cells", Digestive Diseases and Sciences 45(9):1769-1773 (2000).

Chung et al, "Protective effects of hemin and tetrakis(4-benzoic acid)porphyrin on bacterial mutagenesis and mouse skin carcinogenesis induced by 7,12-dimethylbenz[α]anthracene", Mutation Research 472:139-145 (2000).

Obst et al, "*Helicobacter pylori* causes DNA damage in gastric epithelial cells", Carcinogenesis 21(6):1111-1115 (2000).

Patel and Day, "Metalloporphyrin class of therapeutic catalytic antioxidants", TIPS Elsevier Trends Journal 20(9):359-364 (1999).

White et al, "A Highly Stereoselective Synthesis of Epothilone B", J. Org. Chem. 64:684-685 (1999).

Batinic-Haberle et al, "The *Ortho* Effect Makes Manganic *Meso*-Tetrakis-(*N*-Methylpyridinium-2-YL)(MnTM-2-PyP$^{5+}$) A Powerful And Useful Superoxide Dismutase Mimic", Oxygen '97, The 4$^{th}$ Annual Meeting of The Oxygen Society, Council Meeting, The Palace Hotel, San Francisco, California, Nov. 20-24, 1997, —p. 38, Abstract 1-8.

Groves and Marla, "Peroxynitrite-Induced DNA Strand Scission Mediated by a Manganese Porphyrin", J. Am. Chem. Soc. 117(37):9578-9579 (1995).

Beckman et al, "Apparent hydroxyl radical production by peroxynitrite: Implications for endothelial injury from nitric oxide and superoxide", Proc. Natl. Acad. Sci. USA 87:1620-1624 (1990).

Shimanovich et al, "Mn(II)-Texaphyrin as a Catalyst for the Decomposition of Peroxynitrite", J. Am. Chem. Soc. 123:3613-3614 (2001).

El-Far and Pimstone, "Selective in Vivo Tumor Localization of Uroporphyrin Isomer I in Mouse Mammary Carcinoma: Superiority over Other Porphyrins in a Comparative Study", Cancer Research 46:34390-4394 (1986).

Polson et al, "The Effect of Liver Transplantation in a 13-Year-Old Boy with Erythropoietic Protoporphyria", Transplantation 46(3):386-389 (1988).

He et al., "Comparative study of photophysical properities of isomeric tetrapyridyl- and tetra-(N-hexadecypyridiniumyl) porphyrins", Spectrochimica Acta Part A 55:873-880 (1999).

Sorenson, John R.J., "Copper Chelates as Possible Active Forms of the Antiarthritic Agents", Journal of Medicinal Chemistry 19(1):135-148 (1976).

Spasojevic and Batinic-Haberle, "Manganese(III) complexes with porphyrins and related compounds as catalytic scavengers of superoxide", Inorganica Chimica Acta 317:230-242 (2001).

Stralin et al., "Effects of Oxidative Stress on Expression of Extracellular Superoxide Dismutase, CuZnSuperoxide Fibroblast", Biochem. J. 298:347-352 (1994).

Szabo et al., "Evaluation of the relative contribution of nitric oxide and peroxynitrite to the suppression of mitochondrial respiration in immunostimulated macrophages using a manganese mesoporphyrin superoxide dismutase mimetic and peroxynitrite scavenger", FEBS Letters 381:82-86 (1996).

Szabo et al., "Peroxynitrite is involved in the Pathogenesis of the Vascular Contractile and Energetic Failure in Endotoxic Shock", Shock Society Meeting (1996).

Tjahjono et al., "Cationic porphyrins bearing diazolium rings: synthesis and their interaction with calf thymus DNA", Biochemica et Biophysica Acta 1472:333-343 (1999).

Tsan, M-F., "Superoxide Dismutase and Pulmonary Oxygen Toxicity," XP-002074505, pp. 286-290.

Szabo et al., "Part I: Pathogenetic Role of Peroxynitrite in the Development of Diabetes and Diabetic Vascular Complications: Studies With FP15, A Novel Potent Peroxynitrite Decomposition Catalyst", Molecular Medicine 8 (10):571-580 (2002).

Iamamoto, Yassuko, et al. "Iron(III) Porphyrins Atropisomers as Catalysts for Cyclohexane Hydroxylations. A Biomimetical System", *Journal of Inorganic Biochemistry* (1994) 54:55-66.

Perez, J., et al. "Spontaneous reduction of octadecyltetracyanoquinodimethane at the air-water interface in the presence of amphiphilic cations", *Thin Solid Films* (1994) 244:1043-1049.

Iamamoto, Yassuko, et al. "Cationic ironporhpyrins as catalyst in comparative oxidation of hydrocarbons: homogeneous and supported on inorganic matrices systems", *Journal of Molecular Catalysis A: Chemical* (1995) 99:187-193.

Porteau, F., et al. "Molecular engineering at the air-water interface: building up designed supermolecular assemblied with amphiphilic porphyrins", *Molecular Crystals and Liquid Crystals* (1992) 211:193-198.

Porteau, F., et al. "Supermolecular Engineering at the Air-Water Interface: Spatially Controlled Formation of Heterodimers from Amphiphilic Porphyrins and Porphyrazines through Specific Molecular Recognition", *J. Phys. Chem.* (1991) 95:7438-7447.

Miller, A., et al. "Langmuir-Blodgett Films Containing Porphyrins in a Well-Defined Environment", *Thin Solid Films* (1985) 133:83-91.

Ruaudel-Teixier, A., et al. "Langmuir-Blodgett Films of Pure Porphyrins", *Thin Solid Films* (1983) 99:33-40.

* cited by examiner

Mn^III TM-2-PyP^5+          Mn^III TnOct-2-PyP^5+

As the alkyl chains of Mn(III) porphyrins lengthen, the favorable increase in $E_{1/2}$ overcomes the unfavorable steric/electrostatic effects such that the n-octyl is as potent a catalyst of $O_2^-$ dismutation as are the methyl and ethyl compounds.

SUBSTITUTED PORPHYRINS

This application claims priority from Provisional Application No. 60/386,454, filed Jun. 7, 2002, the content of which is incorporated herein by reference.

INTRODUCTION

Low-molecular weight catalytic scavengers of reactive oxygen and nitrogen species, aimed at treating oxidative stress injuries, have been actively sought. Three major groups of manganese complexes have been developed and tested in vitro and in vivo; Mn porphyrins,[1-9] Mn cyclic polyamines[10] and Mn salen derivatives.[11] Based on a structure-activity relationships that we developed for water-soluble MN(III) and Fe(III) porphyrins,[2-4] Mn(III) meso tetrakis(N-methylpyridinium-2-yl)porphyrin (Mn$^{III}$TM-2-PyP$^{5+}$, AEOL-10112) and meso tetrakis(N-ethylpyridinium-2-yl)porphyrins (Mn$^{III}$TE-2-PyP$^{5+}$, AEOL-10113) were proposed and then shown to be potent catalysis for superoxide dismutation.[4,12] The alkyl substitutions at the ortho positions restrict the rotation of the pyridyl rings with respect to the porphyrin plane. Consequently both compounds exist as mixtures of four atropoisomers, all of which were shown to be equally potent catalysts for $O_2^-$ dismutation.[13] These Mn porphyrins also allow SOD-deficient *Escherchia coli* to grow under aerobic conditions,[4,12] and offer protection in rodent models of oxidative stress such as stroke,[14] diabetes,[15] sickle cell disease,[16] and cancer/radiation.[17] The high formal +5 charge of these metalloporphyrins could influence their tissue distribution, transport across biological membranes, and binding to other biomolecules and their low lipophilicities may restrict their protective effects. With the aim of modulating metalloporphyrin subcellular distribution, higher N-alkylpyridylporphyrin analogues (Scheme I) with increased lipophilicity were synthesized. We anticipate that their comparative kinetic and thermodynamic characterization will deepen our insight into the modes of action of porphyrin-based catalytic antioxidants and the mechanisms of oxidative stress injuries.

DETAILED DESCRIPTION OF THE INVENTION

Figure 1:
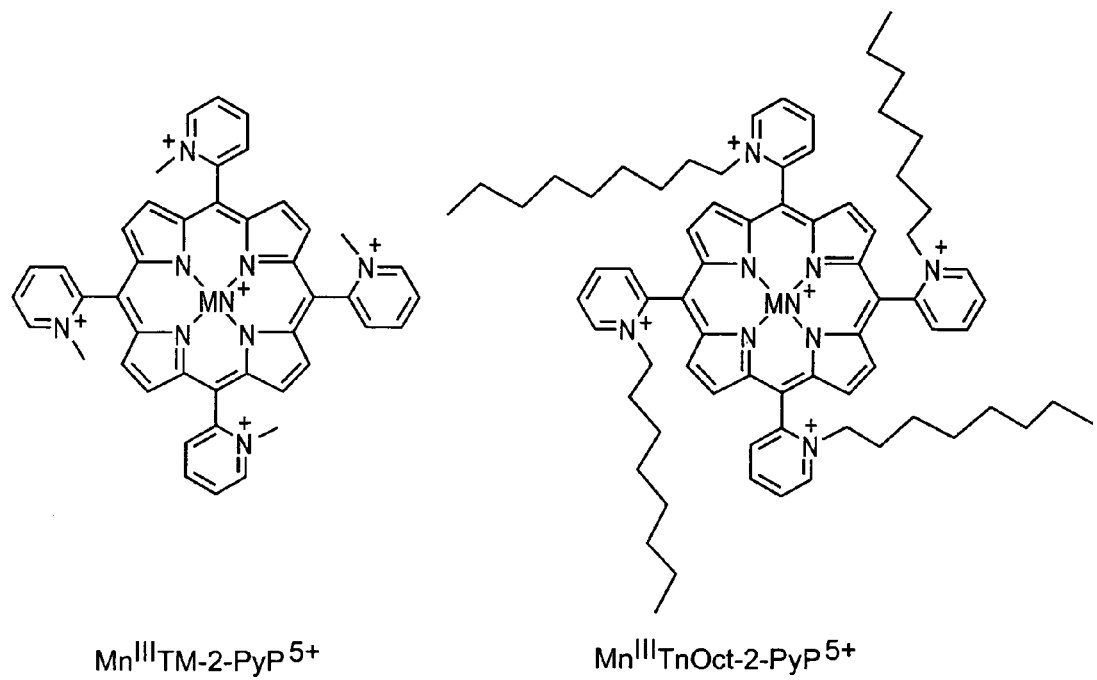
FIG. 1. Structures of the most hydrophilic (Mn$^{III}$TM-2-PyP$^{5+}$) and the most lipophilic (Mn$^{III}$TnOct-2-PyP$^{5+}$) members of the series studied. The αβαβ atropoisomers are shown.
Figure 1:
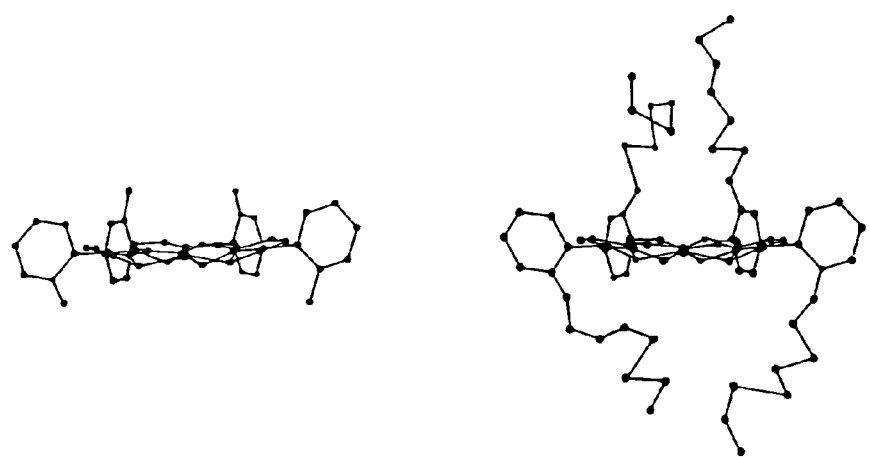

The present invention relates to a compound of formula

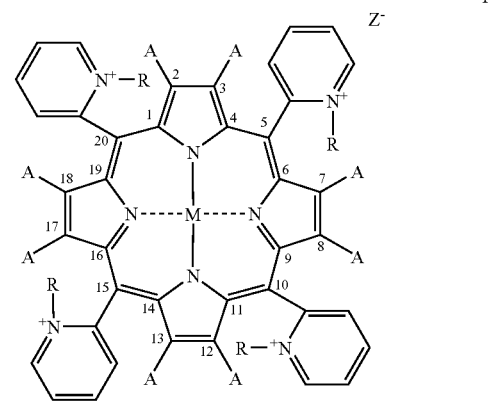

I

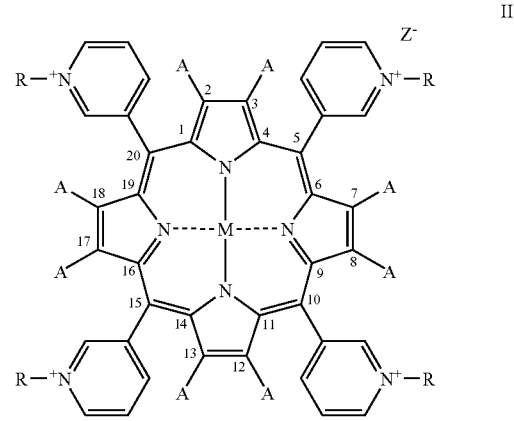

II

-continued

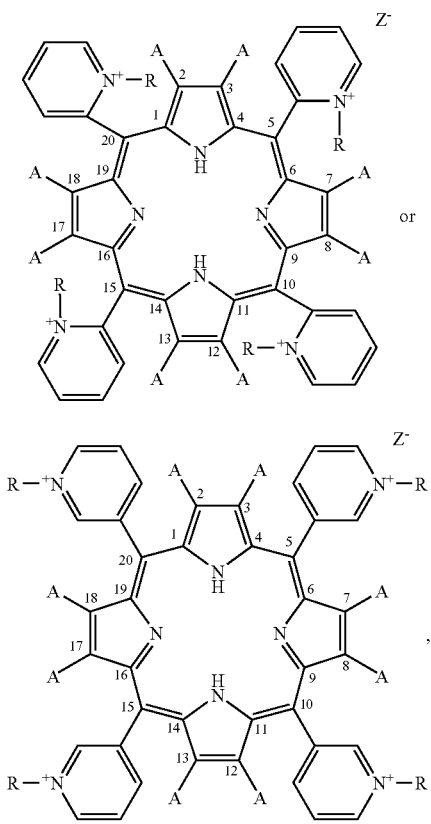

wherein each R is, independently, an C1-C12 alkyl (preferably, a C8 to C12 alkyl), each A is, independently, hydrogen or an electron withdrawing group, M is a metal selected from the group consisting of manganese, iron, copper, cobalt, nickel and zinc, and $Z^-$ is a counterion. In one embodiment, at least one A is a halogen.

The invention further relates to a method of protecting cells (eg mammalian cells) from oxidant-induced toxicity comprising contacting the cells with a protective amount of a compound as described above. The invention further relates to a method of treating a pathological condition of a patient resulting from oxidant-induced toxicity comprising administering to the patient an effective amount of such a compound. The invention also relates to a method of treating a pathological condition of a patient resulting from degradation of NO., comprising administering to the patient an effective amount of a compound as described above. Additionally, the invention relates to a method of treating a patient for inflammatory lung disease comprising administering to the patient an effective amount of a compound as described above. The inflammatory lung disease can be a hyper-reactive airway disease. The disease can be asthma.

The entire content of all documents cited herein are incorporated herein by reference. Also incorporated herein by reference is Batinic-Haberle et al, J. Chem. Soc., Dalton Trans. 2002, 2689-2696.

Also incoprporated by reference is U.S. application Ser. No. 09/880,125, filed Jun. 14, 2001.

EXAMPLE

Experimental

Materials and Methods

General. $MnCl_2 \times 4\ H_2O$, and Baker-flex silica gel IB TLC plates were purchased from J.T. Baker. N,N'-dimethylformamide, ethyl p-toluenesulfonate, 2-propanol (99.5+%), $NH_4PF_6$(99.99%), NaCl, sodium L-ascorbate (99+%) and tetrabutylammonium chloride were from Aldrich, while xanthine, and ferricytochrome c were from Sigma. The n-propyl, n-butyl, n-hexyl and n-octyl esters of p-toluenesulfonic acid were from TCI America. Methanol (anhydrous, absolute), ethanol (absolute), acetone, ethyl ether (anhydrous), chloroform, EDTA and $KNO_3$ were from Mallinckrodt and acetonitrile was from Fisher Scientific. Xanthine oxidase was prepared by R. Wiley and was supplied by K.V. Rajagopalan.[18] Catalase was from Boehringer, ultrapure argon from National Welders Supply Co., and tris buffer (ultrapure) was from ICN Biomedicals, Inc.

$H_2T(alkyl)$-2-$PyP^{4+}$. Tetrakis(2-pyridyl)porphyrin, $H_2T$-2-PyP was purchased from Mid-Century Chemicals, Chicago, Ill. The increased lipophilicity of the n-propyl, n-butyl, n-hexyl, and n-octyl analogues required a slight modification of the synthetic approach used for methyl and ethyl compounds.[4,12] Typically, 100 mg of $H_2T$-2-PyP was dissolved in 20 mL of DMF at 100° C., followed by the addition of 4 mL of the corresponding p-coluenesulfonate. The course of N-alkylation was followed by thin-layer chromatography on silica gel TLC plates using 1:1:8 $KNO_3$-saturated $H_2O:H_2O$:acetonitrile as a mobile phase. While complete N-alkylation is achieved within a few hours for the methyl analogue, the required time gradually increases and it took three and five days to prepare the n-hexyl and n-octyl compounds, respectively. Upon completion, for the methyl, ethyl and n-propyl compounds, the reaction mixture was poured into a separatory funnel containing 200 mL each of water and chloroform and shaken well. The chloroform layer was discarded and the extraction with $CHCl_3$ was repeated several times. The n-butyl, n-hexyl and n-octyl analogues are more lipophilic and tended to remain in the chloroform layer. Therefore, increasing amounts of methanol were added to the water/$CHCl_3$ mixture in order to force the porphyrin into the aqueous/methanol layer. This layer was filtered and the porphyrin was precipitated as the $PF_6^-$ salt by the addition of a concentrated aqueous solution of $NH_4PF_6$. The precipitate was thoroughly washed with 1:1 2-propanol:diethylether in the case of methyl and ethyl compounds and with pure diethylether for the others. The precipitate was then dissolved in acetone, filtered and precipitated as the chloride salt by the addition of tetrabutylammonium chloride dissolved in acetone. The precipitate was washed thoroughly with acetone, and dried in vacuo at room temperature. Elemental analysis: $H_2TnPr$-2-$PyPCl_4 \times 12.5\ H_2O$ ($C_{52}H_{71}N_8O_{12.5}Cl_4$): Found: C, 54.2; H, 6.42; N, 9.91; Cl, 12.04. Calculated: C, 54.20; H, 6.18; N, 9.68; Cl, 12.25. $H_2TnBut$-2-$PyPCl_4 \times 10.5\ H_2O$ ($C_{56}H_{75}N_8O_{10.5}Cl_4$): Found: C, 57.16; H, 6.94; N, 9.513; Cl, 1.77. Calculated: C, 57.10; H, 6.41; N, 9.51; Cl, 12.03. $H_2TnHex$-2-$PyPCl_4 \times 11\ H_2O$ ($C_{64}H_{100}N_8O_{11}Cl_4$): Found: C, 59.19; H, 7.31; N, 8.61; Cl, 11.09. Calculated: C, 59.16; H, 7.751; N, 8.60; Cl, 10.91. $H_2TnOct$-2-$PyPCl_4 \times 13.5\ H_2O$ ($C_{64}H_{121}N_8O_{13.5}Cl_4$): Found: C, 59.37; H, 7.41; N, 7.73. Calculated: C, 59.37; H, 8.37; N, 7.69.

$Mn^{III}T(alkyl)$-2-$PyP^{5+}$. Metalation of the N-alkylated porphyrins was achieved as described previously for the methyl and ethyl compounds.[4,12] Metal incorporation became slower as the alkyl chains lengthened. Under same conditions (20-fold excess metal, 25° C., pH 12.3) it occurs almost instantaneously for methyl and ethyl, within minutes for n-propyl, in ~30 minutes for n-butyl, in ~1 hour with the n-hexyl, and took several hours at 100° C. for the n-octyl porphyrin. The formation of the Mn(I) porphyrin and its oxidation to Mn(III) were clearly distinguishable steps when the n-hexyl and n-octyl analogues were metalated. As was the case with the metal-free ligands, the $PF_6^-$ salts of Mn(III) n-propyl, n-butyl, n-hexyl and n-octyl compounds were washed only with diethylether. Elemental analysis: $Mn^{III}TnPr-2-PyPCl_5 \times 11.5\, H_2O$ ($MnC_{52}H_{75}N_8O_{11.5}Cl_5$: Found: C, 50.90; H, 6.07; N, 9.27; Cl, 13.48. Calculated: C, 50.85; H, 6.16; N, 9.12; Cl, 14.43. $Mn^{III}TnBut-2-PyPCl_5 \times 12.5\, H_2O$ ($MnC_{56}H_{85}N_8O_{12.5}Cl_5$): Found: C, 51.58; H, 6.33; N, 9.55; Cl, 15.53. Calculated: C, 51.64; H, 6.58; N, 8.60; Cl, 13.61. $Mn^{III}TnHex-2-PyPCl_5 \times 10.5\, H_2O$ ($MnC_{64}H_{97}N_8O_{12.5}Cl_5$): Found: C, 55.64; H, 7.14; N, 8.23; Cl, 12.60. Calculated: C, 55.76; H, 7.09; N, 8.13; Cl, 12.86. $Mn^{III}TnOct-2-PyPCl_5 \times 10\, H_2O \times 2.5\, NH_4Cl$ ($MnC_{64}H_{122}N_{10.5}O_{10}Cl_{7.5}$): Found: C, 53.56; H, 7.13; N, 9.12; Cl, 16.84. Calculated: C, 53.53; H, 7.60; N, 9.10; Cl, 16.46.

Thin-layer chromatography. All ligands and their Mn(III) complexes were chromatographed on silica gel TLC plates using 1:1:8 $KNO_3$-saturated $H_2O$:$H_2O$: acetonitrile. The atropoisomers could not be separated for the methyl[19] and ethyl analogues,[24] they begin to separate for the n-propyl and n-butyl species and were clearly resolved with the n-hexyl and n-octyl compounds.

Uv/vis spectroscopy. The uv/vis spectra were taken on a Shimadzu UV-2501 PC spectrophotometer at 25° C. The proton dissociation constants ($pK_{a2}$), were determined spectrophotometrically at 25° C., at an ionic strength of 0.1 M ($NaOH/NaNO_3$), as previously described.[4]

Electrochemistry. Measurements were performed on a CH Instruments Model 600 Voltammetric Analyzer.[3,4] A three-electrode system in a small volume cell (0.5 mL to 3 mL), with a 3 mm-diameter glassy carbon button working electrode (Bioanalytical Systems), plus the Ag/AgCl reference and Pt auxilliary electrodes was used. Solutions contained 0.05 M phosphate buffer, pH 7.8, 0.1 M NaCl, and 0.5 m/M metalloporphyrin. The scan rates were 0.01-0.5 V/s, typically 0.1 V/s. The potentials were standardized against the potassium ferrocyanide/ferricyanide[20] and/or against $Mn^{III}TE-2-PyP^{5+}$. All voltammograms were reversible.

Electrospray mass spectrometry. ESMS measurements were performed on a Micromass Quattro LC triple quadrupole mass spectrometer equipped with a pneumatically assisted electrostatic ion source operating at atmospheric pressure. Typically, the 0.5 mM 50% aqueous acetonitrile solutions of chloride salts of metal-free porphyrins or their Mn(III) complexes were introduced by loop injection into a stream of 50% aqueous acetonitrile flowing at 8 μL/min. Mass spectra were acquired in continuum mode, scanning from 100-500 m/z in 5 s, with cone voltages of 20 V and 24 V. The mass scale was calibrated using polyethylene glycol.

Figure 2A:
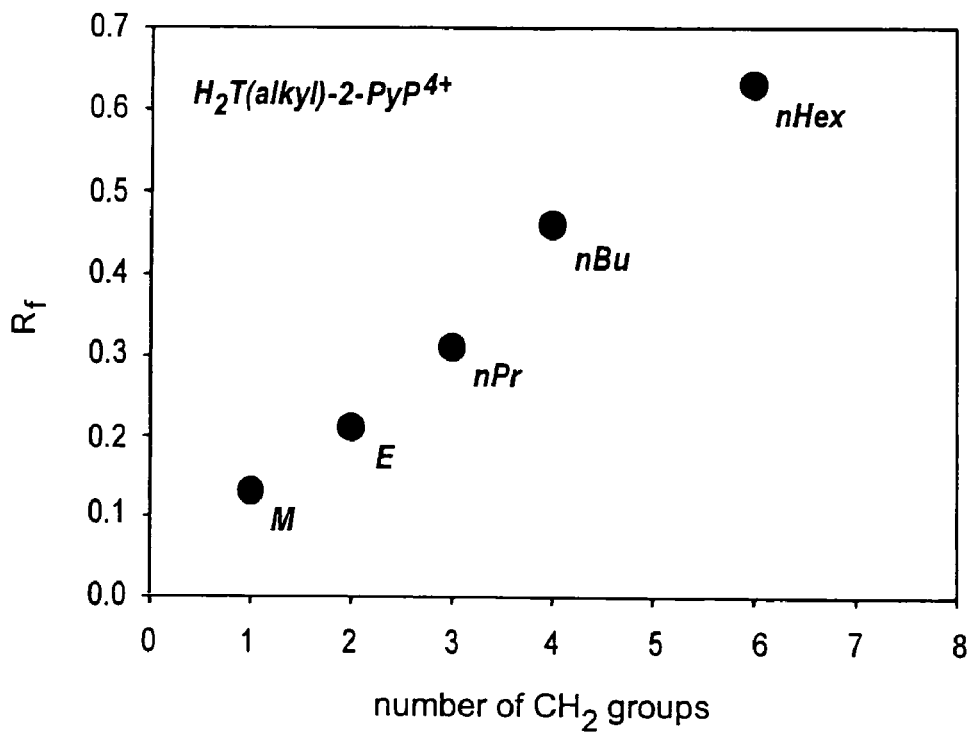
FIG. 2. The lipophilicity, $R_f$ of $H_2$T(alky)-2-PyP$^{4+}$ (A) and Mn$^{III}$T(alkyl)-2-PyP$^{5+}$ compounds (B) vs the number of CH$_2$ groups.
Figure 2B:
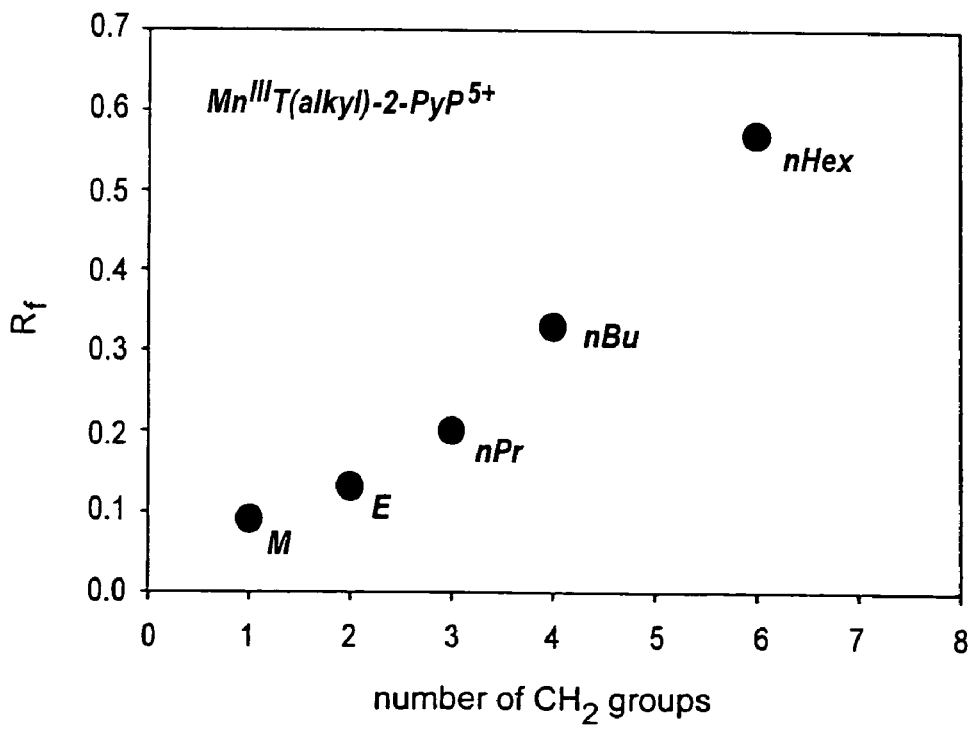

Catalysis of $O_2^-$ dismutation. We have previously shown that the $O_2^-$/cytochrome c reduction assay gives the same catalytic rate constants as does pulse radiolysis for $Mn^{III}TE-2-PyP^{5+}$, $\{Mn^{III}BVDME\}_2$, $\{Mn^{III}BV\}_2$ and $MnCl_2$.[21] Therefore the convenient cytochrome c assay was used to characterize the series of Mn(III) N-alkylpyridylporphyrins. The xanthine/xanthine oxidase reaction was the source of $O_2^-$ and ferricytochrome c was used as the indicating scavenger for $O_2^-$.[22] The reduction of cytochrome c was followed at 550 nm. Assays were conducted at (25±1) ° C., in 0.05 M phosphate buffer, pH 7.8, 0.1 mM EDTA, in the presence and absence of 15 μg/mL of catalase. Rate constants for the reaction of metalloporphyrins with $O_2^-$ were based upon competition with 10 μM cytochrome c, $k_{cyt\, c}$=2.6×10$^5$ M$^{-1}$ s$^{-1}$ as described elsewhere.[21] The $O_2^-$ was produced at the rate of 1.2 μM per minute. Any possible interference through inhibition of the xanthine/xanthine oxidase reaction by the test compounds was examined by following the rate of urate accumulation at 295 nm in the absence of cytochrome c. No reoxidation of cytochrome c by the metalloporphyrins was observed Results Thin Layer Chromatography. The increase in the length of the alkyl chains is accompanied by an increase in the lipophilicity of the compounds as indicated by the increase in the retention factor $R_f$ (porphyrin path/solvent path) (Table 1, FIG. 2). The apparent lag that was observed in the case of shorter chains with Mn(III) complexes (FIG. 2B), is presumably due to their higher overall formal charge (+5 for the Mn(III) complexes, +4 for the ligand). As the chains lengthen, their contribution to the overall lipophilicity increases, and eventually the n-octyl porphyrin and its Mn(III) complex are more alike in $R_f$ than are methyl analogues.

Uv/vis spectroscopy. Molar Absorptivies. The porphyrins obeyed the Beer-Lambert law from 10$^{-7}$ M to 10$^{-5}$ M, and the uv/vis data are given in Table 2. As the length of alkyl chains increased from methyl to n-butyl a red shift of the Soret absorption maxima was generally observed, as well as an increase in the molar absorptivities, and these effects plateau beyond buryl compound. Such trends may be understood in terms of the interplay of porphyrin nucleus distortion (red shifts) and the electron-withdrawing (blue shifts) effect of the N-alkylpyridyls groups.[12,23]

Metalation behavior and proton dissociation constants. The rates of Mn$^{2+}$ incorporation at pH ~12.3 decreased with an increase in chain length. The same was found for the kinetics of Zn$^{2+}$ and Cu$^{2+}$ insertion into these compounds below pH 7, where the kinetics were first order in metal and porphyrin concentration.[24] Since the free-base porphyrin $H_2P^{4+}$ reactants were mixtures of the four atropoisomers, each isomer has a similar metalation rate constant. As noted before for both water soluble and insoluble porphyrins, compounds with substituents in the ortho positions tend to metalate more slowly than derivatives with the same groups in the meta or para positions.[25-34]

The proton dissociation constants, $K_{a2}$ and $K_{a3}$ are defined as follows:

Figure 3A:
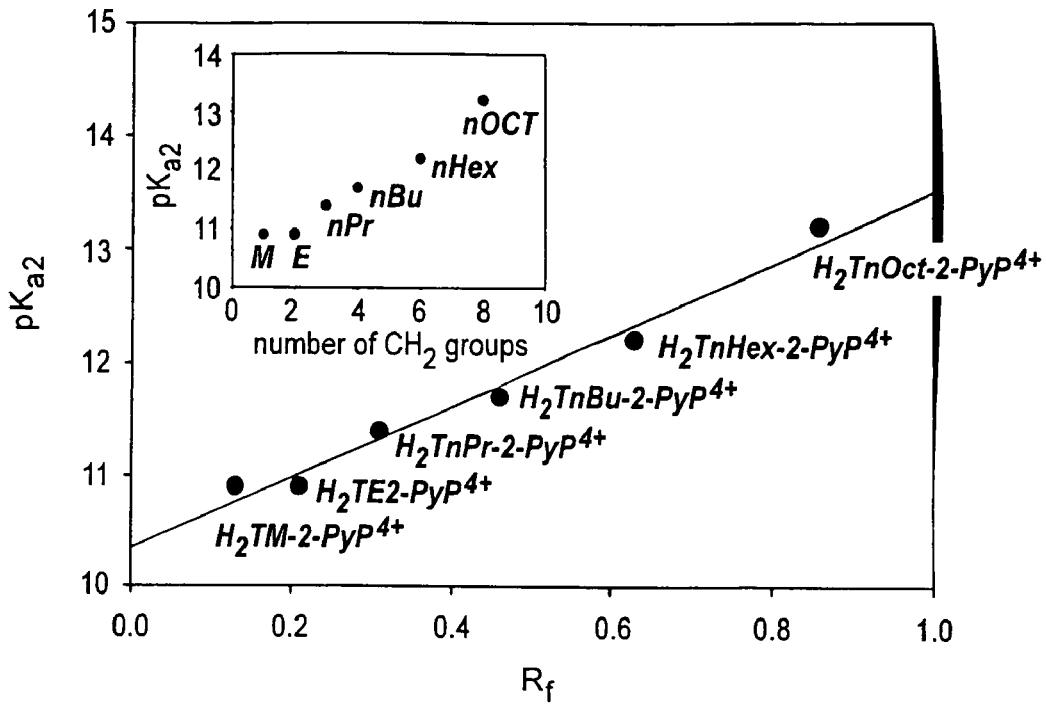
FIG. 3. Proton dissociation constants pK$_{a2}$ of the metal-free porphyrins, $H_2$T(alkyl)-2-PyP$^{4+}$ (A), and the metal-centered redox potentials E$_{1/2}$ for the Mn(III)/Mn(II) couple of Mn$^{III}$(alkyl)-2-PyP$^{5+}$ porphyrins (B) as a function of $R_f$. Inserts: pK$_{a2}$ (FIG. 3A) and E$_{1/2}$ (FIG. 3B) vs the number of CH$_2$ groups.

The $pK_{a2}$ values for the N-alkylpyridyl series are given in Table 1. As the alkyl chains lengthen the porphyrins become less hydrated and the separation of charges (eq [1]) becomes less favorable, ie. $pK_{a2}$ increases (FIG. 3 insert). FIG. 3A shows the linear relationship between $pK_{a2}$ and $R_f$.

Equilibrium constants $pK_{a3}$ for reaction [2] are 1.8 for the meta $H_2TM-3-PyP^{4+}$, 1.4 for the para $H_2TM-4-PyP^{4+}$, and —0.9 for ortho $H_2TM-2-PyP^{4+}$.[4,25] While the meta and para N-methylpyridylporphyrins are mixtures of protonated $H_3P^{5+}$ and $H_4P^{6+}$ species in 1.0 M HCl, the ortho substituted $H_2TM-2-PyP^{4+}$ to $H_2TnOct-2-PyP^{4+}$ compounds remain as the unprotonated free base $H_2P^{4+}$ in 1.0 M HCl and in 1.0 M HNO$_3$. With ortho, meta and para N-methylpyridylporphyrins the $pK_{a2}$ increases as the $pK_{a3}$ increases.

The half-lives for the acid and anion-catalyzed removal of zinc from Zn N-methylated derivatives[35] in 1.0 M HNO$_3$ were 89 s for the meta, 165 s for the para, and 19 hours for the ortho ZnTM-2-PyP$^{4+}$. No indication of zinc loss was found within a week for the ZnTnHex-2-PyP$^{4+}$ compound.[36] Similar behavior is found in 1.0 M HCl, with $t_{1/2}$ ranging from 21 s for the meta methyl to 76 hours for ZnTnOct-2-PyP$^{4+}$.[24] In accord are the observations that when solid MnTnHex-2-PyP$^{5+}$ was dissolved in 12 M HCl, the spectra did not change within 3 months, while over 50% of the Mn from Mn$^{III}$TM-2-PyP$^{5+}$ species was lost within a month. In addition to porphyrin ring distortion,[29-32] the steric hindrance and solvation effects imposed by the progressively longer alkyl chains may also contribute to the differences in metaladon/demetalation behavior.

Due to their high metalcentered redox potentials, the Mn(III) meso tetrakis ortho N-alkylpyridylporphyrins in vivo will be readily reduced with cell reductants such as ascorbic acid.[2,3,12] The reduced Mn(II) porphyrins will also be transiently formed in the catalysis of $O_2^-$ dismutation. Therefore, we also examined the behavior of the reduced and more biologically relevant Mn$^{II}$T(alkyl)-2-PyP$^{4+}$ compounds. We compared the methyl, n-hexyl and n-octyl derivatives (6 μM) aerobically and anaerobically in the presence of a 70-fold excess of ascorbic acid (pH 7.8, 0.1 M tris buffer) and in the presence and absence of a 150-fold excess of EDTA. Under anaerobic conditions both Mn(II) porphyrins were stable to Mn loss and porphyrin decomposition inside 24 hours. Aerobically, ~40% of Mn methyl but none of the Mn n-hexyl and n-octyl compounds underwent degradation within 125 min. The absorption spectral changes indicate that the degradation occurred through the Mn porphyrin catalyzed reduction of oxygen by ascorbate resulting in the formation of $H_2O_2$. The peroxide in turn causes porphyrin destruction. These observations are consistent with previous results which indicate that a more electron rich compound (Mn$^{II}$TM-2-PyP$^{4+}$) reduces $O_2$ faster than does a more electron deficient species (Mn$^{II}$TnOct-2-PyP$^{4+}$).[2,3] EDTA did not significantly influence porphyrin degradation or Mn loss.

Figure 3B:
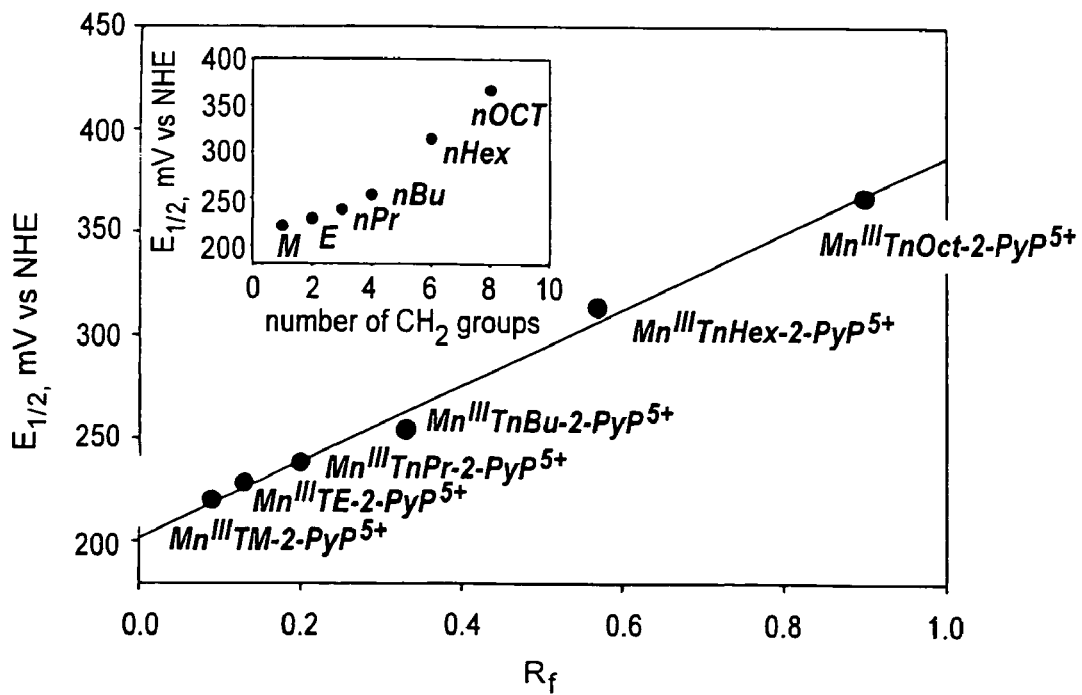
Figure 6:
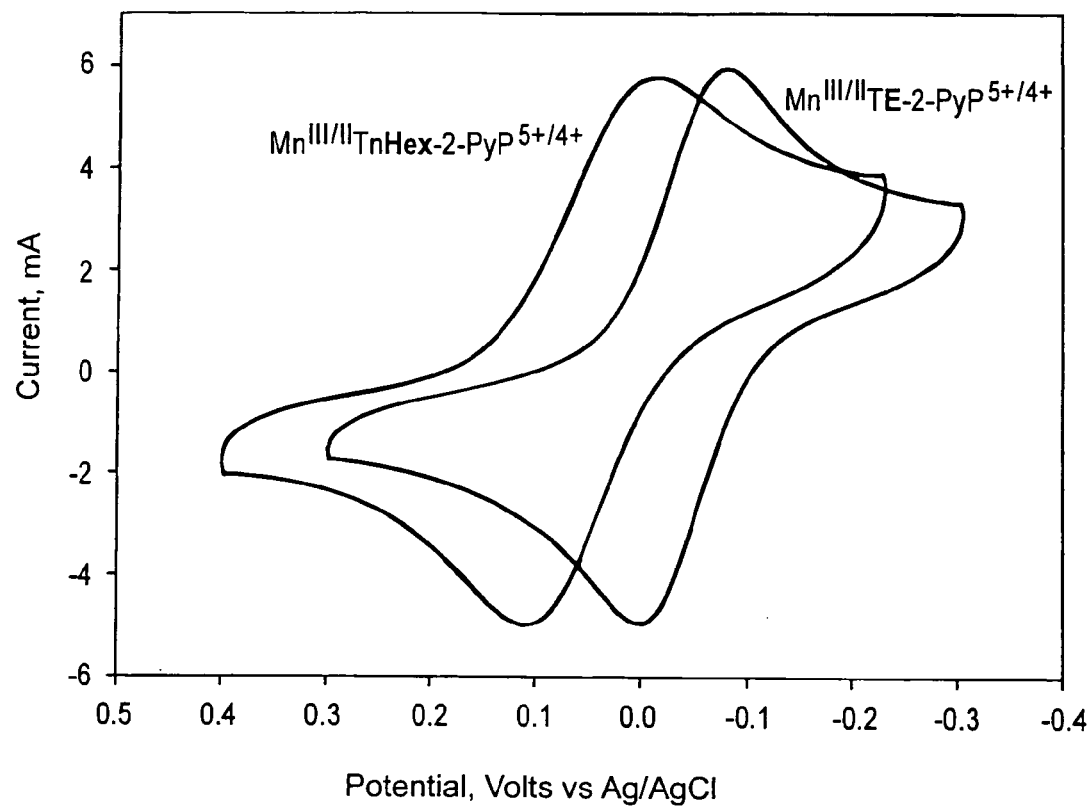
FIG. 6. Cyclic voltammetry of 0.5 mM Mn$^{III}$TE-2-PyP$^{5+}$ and Mn$^{III}$TnHex-2-PyP$^{5+}$ porphyrins in a 0.05 M phosphate buffer (pH 7.8, 0.1 M NaCl) at a scan rate of 0.1 V/s.

Electrochemistry. Cyclic voltammetry of the Mn(III) porphyrins shows a reversible voltammogram that we ascribe to the Mn(III)/Mn(II) redox couple. The metal-centered redox potentials, $E_{1/2}$ are in Table 1 and the representative voltammograms of the Mn$^{III/II}$TE-2-PyP$^{5+/4+}$ and Mn$^{III/II}$TnHex-2-PyP$^{5+/4+}$ compounds are shown in the Supporting Material, FIG. 6. Both lipophilicity (FIG. 2B) and $E_{1/2}$ (FIG. 3B, insert) increase exponentially with the number of $CH_2$ groups in the alkyl chains. Consequently, the increase in $E_{1/2}$ is a linear function of $R_f$ (FIG. 3B).

Electrospray mass spectrometry. The ESMS proved to be a valuable tool for accessing the properties of the free base porphyrins and their Mn complexes whereby the impact of structure on salvation, ion-pairing, redox properties, protonation/deprotonation, dealkylation, and catalytic properties are clearly depicted.

Figure 7:
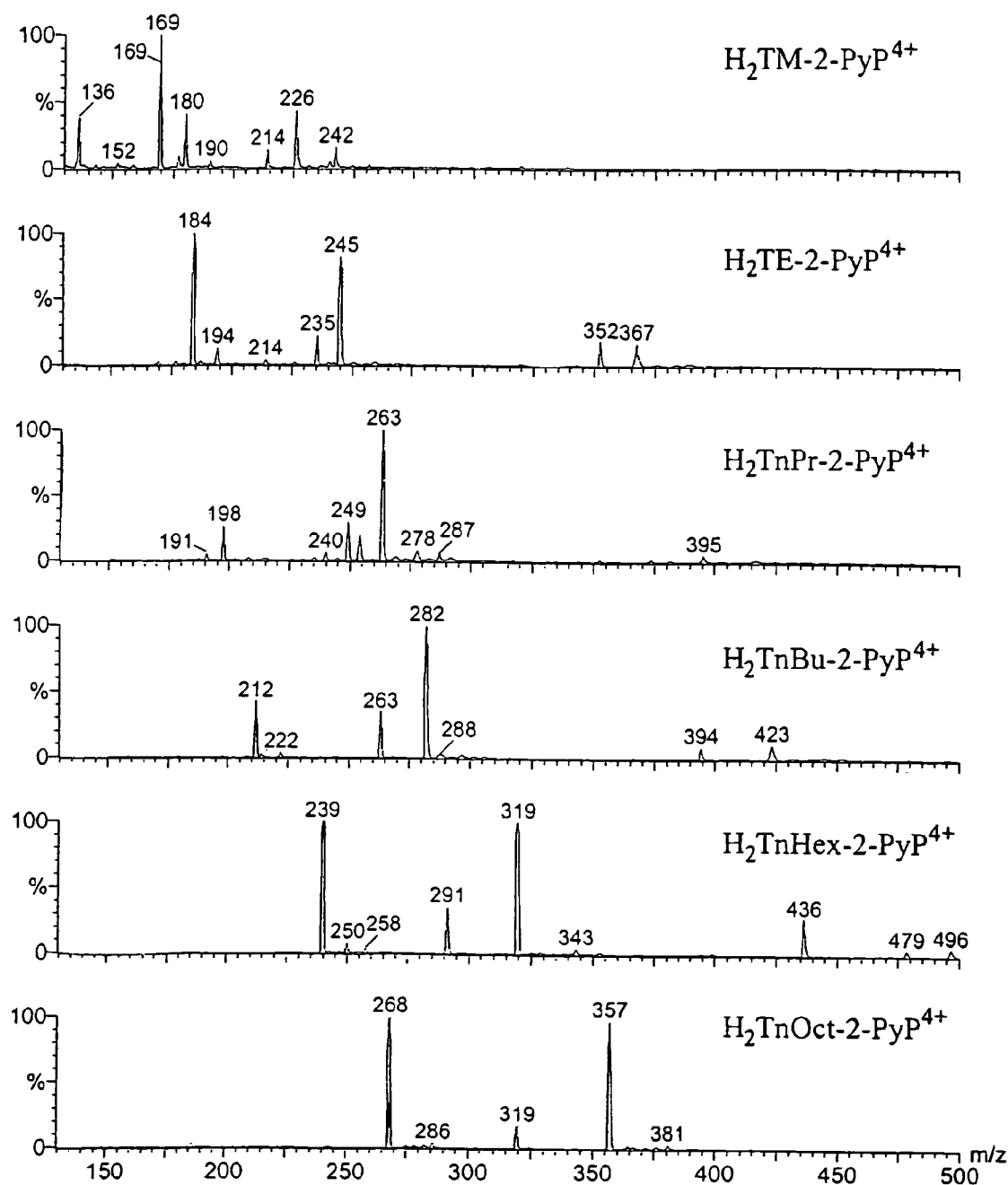
FIG. 7. Electrospray mass spectrometry of 0.5 mM solutions of $H_2$T(alkyl)2-PyP$^{4+}$ compounds in 1:1 water: acetonitrile at a cone voltage of 20 V.

$H_2T$(alkyl)-2-PyP$^{4+}$. The ESMS of the metal-free porphyrins obtained at the low cone voltage of 20 V showed dominant molecular ions assigned to $H_2P^{4+}/4$ and/or its mono-deprotonated analogue, $H_2$-$P^{4+}$-$H^+/3$ (Table 3, FIG. 7). Negligible double deprotonation ($H_2P^{4+}$-$2H^+/2$) was noted. Only $H_2TM$-2-PyP$^{4+}$ gave rise to a high-intensity $H_2P^{4+}$+$H^+/5$ peak.

The ESMS shows a pronounced decrease in solvation by acetonitrile as the alkyl chains lengthen. Compared to the base peak, the relative intensities of the mono-solvated molecular ions range from 40% for methyl, 15% for ethyl, and <10% for the higher analogues. Only with the n-hexyl and n-octyl porphyrins are small peaks (<5%) from ions associated with chloride found.

Figure 8:
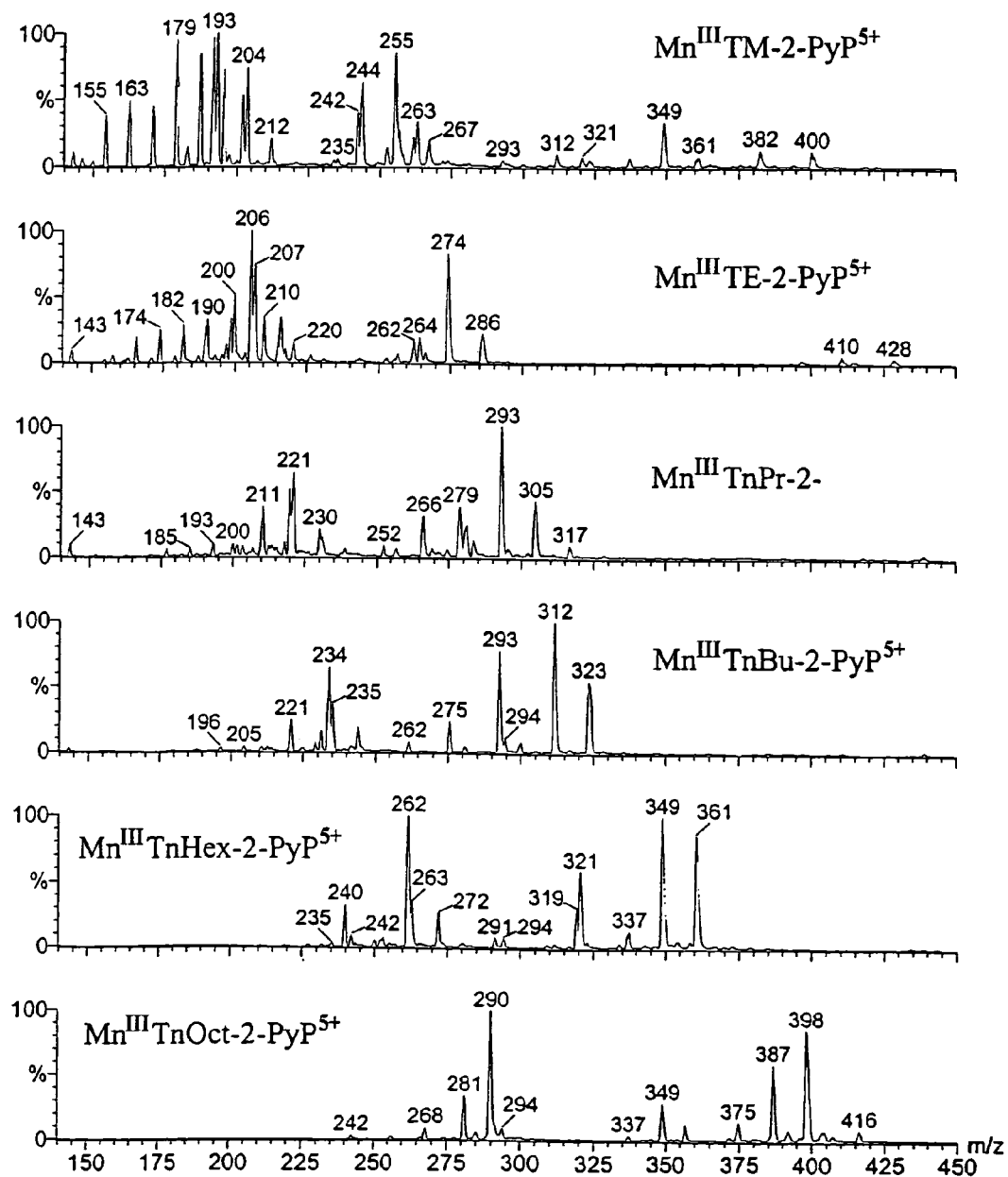
FIG. 8. Electrospray mass spectrometry of 0.5 mM solutions of Mn$^{III}$T(alkyl)2-PyP$^{5+}$ compounds in 1:1 water: acetonitrile at a cone voltage of 20 V.
Figure 9:
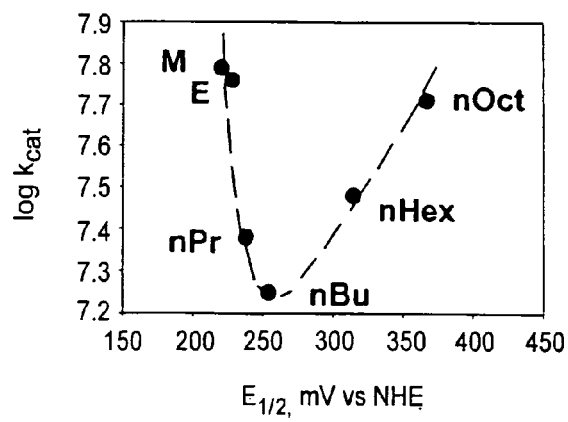
FIG. 9. As the slkyl chains of Mn(III) porphyrins lengthen, the favorable increase in E$_{1/2}$ overcomes the unfavorable steric/electrostatic effects such that the n-octyl is as potent a catalyst of O$_2$ dismutation as are the methyl and ethyl compounds.

From methyl to n-butyl, the ratio of the molecular ion to mono-deprotonated ion peaks decreases, consistent with the trend in p$K_{a2}$. Thus, the base peak for methyl is that of the molecular ion, while the base peak for the n-propyl and n-butyl porphyrins is the mono-deprotonated ion. This p$K_{a2}$ trend is overcome by the higher lipophilicities of the n-hexyl and n-octyl compounds, where roughly equal-intensity molecular ion (100%) and mono-deprotonated ion (98%) peaks are observed. The loss of one alkyl group ($H_2P^{4+}$-$a^+/3$) was noted for all derivatives (except for the methyl), and either no or negligible loss of a second alkyl group ($H_2P^{4+}$-$2a^+/2$) was found Mn$^{III}$T(alkyl)-2-PyP$^{5+}$. The ESMS of the Mn(III) complexes was done at a lower cone voltage (20 V) than in our previous study (30-58 V).[37] Therefore, less fragmentation occurs and more solvent-associated and ion-paired species could be observed (Table 4, FIG. 8). Solvation and ion pairing are more pronounced when compared with the metal-free ligands. The more lipophilic Mn(C) porphyrins are more easily desolvated in the electrospray ionization source. In accordance with our previous observations, the ESMS also clearly reflects the redox properties of these compounds.[37,38] The higher the $E_{1/2}$ the more reduced porphyrins are noted. Species solvated with acetonitrile or associated with chloride were observed with both Mn(III) and Mn(II) compounds. Two chlorides were associated only with Mn(III) porphyrins.

In the ESMS of the n-hexyl and noctyl porphyrins we observed strong signals at m/z 337 and 375 that are assigned to compounds doubly reduced either at the metal (Mn$^{I}$P$^{3+}$/3) or at both the metal and porphyrin ring (Mn$^{II}$P$^{3+}$/3). Such doubly reduced manganese porphyrins should have a higher tendency to lose the metal, and indeed peaks for the metal-free species were found for the n-hexyl and n-octyl derivatives, while only traces of doubly reduced and demetalated species were found for n-butyl.

The ESMS behavior of Mn porphyrins changes sharply once the alkyl chains lengthen beyond butyl, as observed with corresponding metal-free analogues. No loss of methyl groups was detected.[37] As the chains lengthen up to butyl the loss of an alkyl group from Mn(III) and Mn(II) porphyrins becomes more pronounced and then the tendency decreases with n-hexyl and n-octyl. The same trend, but of lower intensity was noted for the loss of two alkyl groups. The ratio of mono-chlorinated Mn(III) to mono-chlorinated Mn(II) species decreases from methyl to n-butyl and then increases up to n-octyl. Thus the base peak of the methyl and ethyl porphyrins relates to Mn$^{III}$P$^{5+}$+Cl$^-$/4, while for the n-propyl and n-butyl derivatives it relates to Mn$^{II}$P$^{4+}$+Cl$^-$/3. Yet, with the n-hexyl, the Mn$^{III}$P$^{5+}$+Cl$^-$/4 and Mn$^{II}$P$^{4+}$+Cl$^-$/3 peaks are both of 100% intensity, and the di-chlorinated species (Mn$^{III}$P$^{5+}$+2Cl$^-$/3) is of 86% intensity. With the n-octyl analogue, the mono- and di-chlorinated species give rise to 100% Mn$^{III}$P$^{5+}$+Cl$^-$/4 and 89% Mn$^{III}$P$^{5+}$+2Cl$^-$/3 peaks, and the third most intense (59%) signal relates to Mn$^{II}$P$^{4+}$+Cl$^-$/3. The lack of significant association of metal-free porphyrins with chloride observed here and elsewhere,[37] strongly supports the idea that chloride is bound to the metal. Furthermore, at the same cone voltage, the base peak of ortho MnTM-2-PyP$^{5+}$ is the mono-chlorinated species, which was only 35% for para isomer. This suggests that the longer the chains, the more defined the cavity, which can hold up to two chloride ions, and the more stable is the Mn(III) state. While a species bearing two chlorides is hardly noted in Mn$^{III}$TM-2-PyP$^{5+}$, it is the second major peak in the ESMS of Mn$^{III}$TnOct-2-PyP$^{5+}$.

Catalysis of $O_2^-$ dismutation. None of the parent metal-free porphyrins exhibit any $O_2^-$ dismuting activity. All of the manganese compounds are potent catalysts of $O_2^-$ dismutation with log $k_{cat}$ between 7.79 and 7.25. As shown in Table 1, log $k_{cat}$ decreases from methyl to n-butyl and then increases, making n-octyl and methyl of comparable antioxidant potency.

Discussion

When designing metalloporphyrin SOD mimics we are aiming at approximating the redox properties of the enzyme active site. Superoxide dismutases catalyse the dismutation (disproportionation) of $O_2^-$ to $H_2O_2$ and $O_2$ at ~+300 V vs NHE (pH 7.0).[39,40] This potential is roughly midway (+360 mV vs NHE) between the potential for the reduction (+890 V vs NHE)[41] and the oxidation of $O_2^-$ (−160 V vs )[41] thus providing an equal driving force for both half-reactions in the catalytic cycle. The $O_2^-$ dismutation by CuZn—SOD occurs with catalytic rate constant, $k_{cat}=k_{red}=k_{ox}=2\times10^9$ $M^{-1}$ $s^{-1}$ (log $k_{cat}=9.3$).[42-44]

Figure 4A:
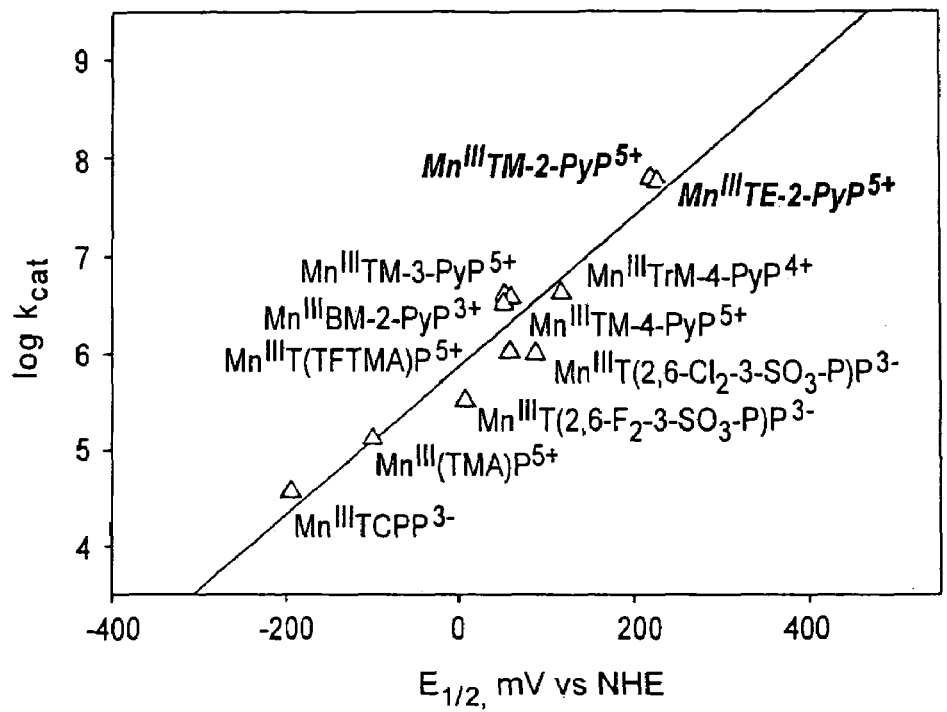
FIG. 4. The reactivity of water-soluble Mn(III) porphyrins (A) (ref 4) and Mn$^{III}$T(alkyl)-2-PyP$^{5+}$ porphyrins (B) as catalysts for $O_2^-$ dismutation, expressed in terms of log k$_{cat}$ vs E$_{1/2}$.

We previously demonstrated a structure-activity relationship between log $k_{cat}$ and the metal-centered $E_{1/2}$ of the Mn(III)/Mn(II) couple for a variety of water-soluble meso substituted porphyrins (FIG. 4A).[2-4] Electron-withdrawing substituents on the porphyrin ring shift $E_{1/2}$ towards more positive values resulting in higher values for $k_{cat}$.[2-4] Each 120 mV increase in $E_{1/2}$ gave a 10-fold increase in $k_{cat}$,[4] consistent with the Marcus equation[45] for outer-sphere electron transfer reactions (FIG. 4A). The Marcus equation is valid as long as one of the two steps in the catalytic dismutation cycle is

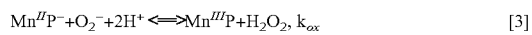

rate-limiting.

On the basis of such structure-activity relationships, the ortho isomers of Mn(III) meso tetrakis N-methyl- and N-ethylpyridylporphyrins were tested and proved to be potent catalysts of $O_2^-$ dismutation. Their log $k_{cat}$ values are 7.79 and 7.76 and they operate at potentials (+220 and +228 V) similar to the potential of the enzyme itself. These two metalloporphyrins also exhibit protection in in vivo models of oxidative stress injuries.[14-17] We have now extended our work to a series of $Mn^{III}T(alkyl)$-2-$PyP^{5+}$ compounds where alkyl is methyl, ethyl, n-propyl, n-butyl, n-hexyl, and n-octyl (FIG. 1). The significant differences in lipophilicity along the series (FIG. 2A), with retention of catalytic potency (Table 1), might lead to favorably selective subcellular distributions of these new $Mn^{III}T(alkyl)$-2-$PyP^{5+}$ compounds and hence broader their utility.

Figure 5:
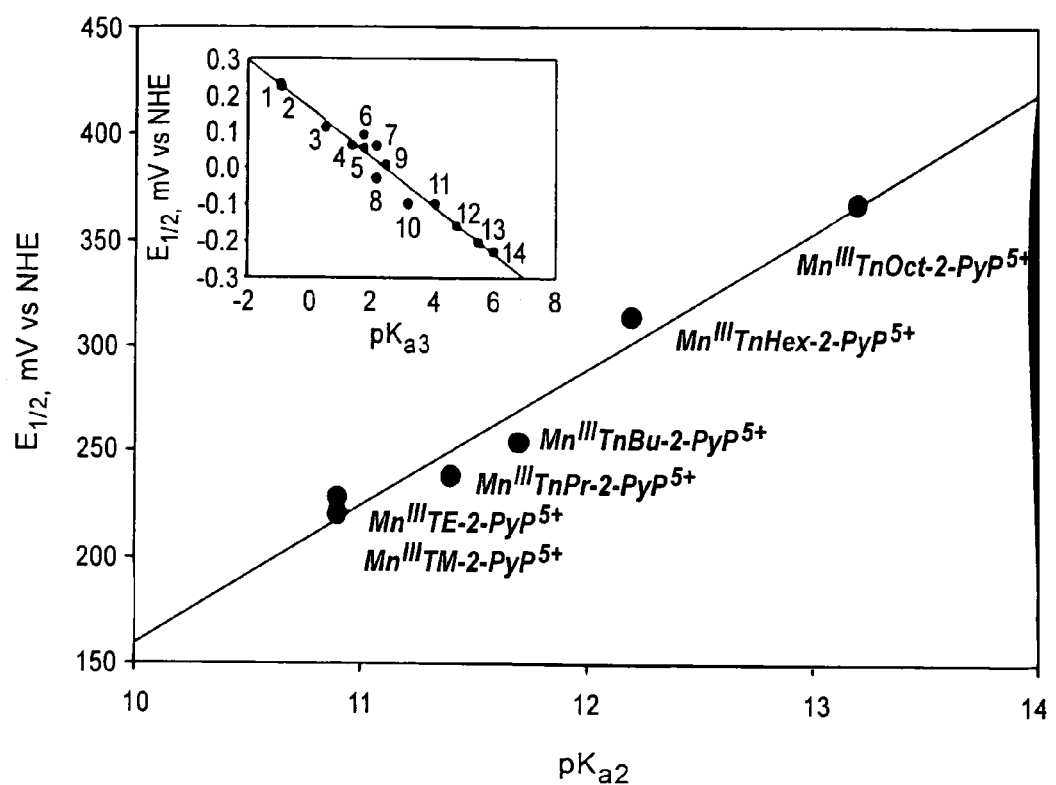
FIG. 5. E$_{1/2}$ for the Mn(III)/Mn(II) couple of Mn$^{III}$T(alkyl)-2-PyP$^{5+}$ porphyrins vs pK$_{a2}$ of the corresponding metal-free ligands. Insert: E$_{1/2}$ of water-soluble Mn(III) porphyrins vs pK$_{a3}$ (data from ref 4); Mn$^{III}$TE-2-PyP$^{5+}$ (1), MnTM-2-PyP$^{5+}$ (2), MnPTrM-2-PyP$^{4+}$ (3), Mn$^{III}$TM-4-PyP$^{5+}$ (4), Mn$^{III}$TM-3-PyP$^{5+}$ (5), Mn$^{III}$T(2,6-Cl$_2$-3-SO$_3$-P)P$^{3-}$ (6), Mn$^{III}$T(TFTMA)P$^{5+}$ (7), Mn$^{III}$T(αααα-2-MINP)P$^{5+}$ (8), Mn$^{III}$T(2,6-Cl$_2$-3-SO$_3$-P)P$^{3-}$ (9), MN$^{III}$T(2,4,6-Me$_3$-3,5-(SO$_3$)$_2$-P)P$^{7-}$ (10), Mn$^{III}$(TMA)P$^{5+}$ (11), MnTSPP$^{3-}$ (12), MnTCPP$^{3-}$ (13), Mn$^{III}$hematoP$^-$ (14).

$E_{1/2}$ vs $pK_{a2}$. We did not expect a profound change in $E_{1/2}$ along the series based on the fact that the increase in alkyl chain length from methyl to n-hexyl is without effect on the basicity of alkylamines.[46] However, we found that the metal-centered redox potentials varied from +220 mV for methyl to +367 mV (vs NHE) for the n-octyl compound. Such an increase in $E_{1/2}$ may originate from progressively unshielded positive charges at pyridyl nitrogens which would then exert stronger electron-withdrawing effect on the coordinated Mn as the compounds increase in lipophilicity. This reasoning is supported by the ESMS data (Table 4, FIG. 8) which show that the susceptibility to desolvation is accompanied by a greater preponderance of reduced Mn(II) porphyrin ions as the alkyl chains of the Mn complexes lengthen. We have previously reported[4] that mainly electronic effects determine the relation between the $pK_a$ of the metal-free porphyrin and the $E_{1/2}$ of the corresponding metal complex such that the decrease in $pK_{a3}$ is accompanied by a linear increase in $E_{1/2}$ (FIG. 5, insert). However as the compounds become increasingly more lipophilic, the lack of solvation disfavors separation of charges (higher $pK_{a2}$ values), while the electron-withdrawing effects of the positively charged pyridyl nitrogens are enhanced. Thus the electronic $pK_{a2}$ effects are overcome by solvation/steric effects resulting in an inverted trend, i. e. the $E_{1/2}$ now increases in a linear fashion with an increase in $pK_{a2}$ (FIG. 5).

Figure 4B:
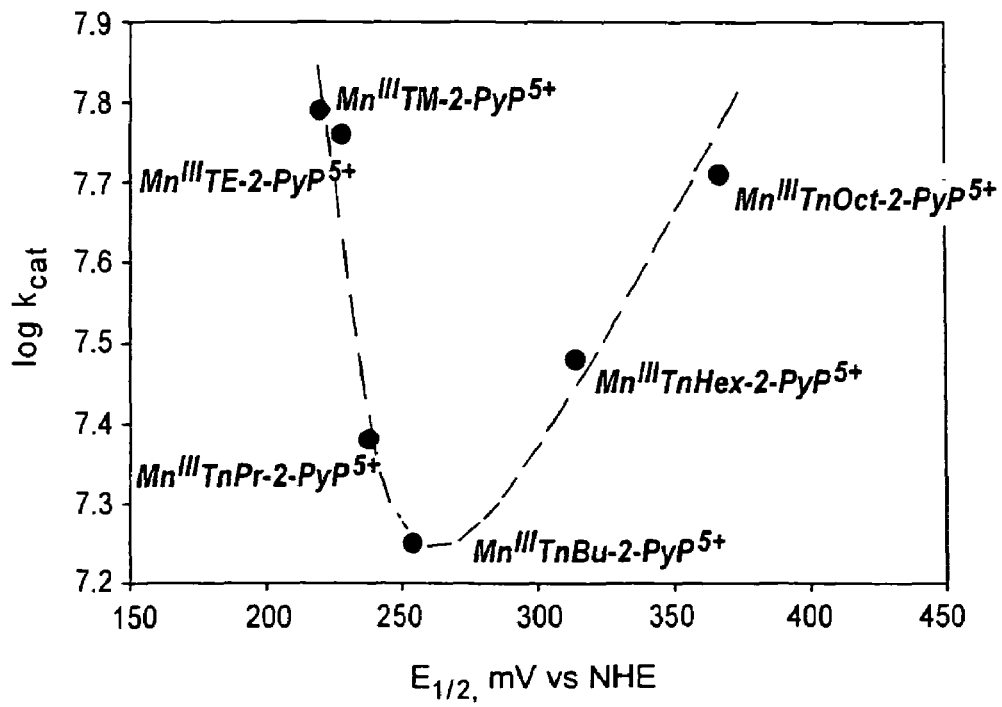

Log $k_{cat}$ vs $E_{1/2}$. Based on a previously established structure-activity relationship for water-soluble Mn(III) porphyrins,[4] we expected the 147 mV increase in $E_{1/2}$ to be accompanied by a ~12-fold increase in $k_{cat}$ (FIG. 4A).[4] We actually found that $k_{cat}$ decreased from methyl to n-butyl, and then increased by the same factor of ~3 to n-octyl (Table 1, FIG. 4B). One explanation is that the Mn porphyrins are solvated to different extents, as indicated by the ESMS data, and this in turn affects the magnitude of $k_{cat}$. The trend in $k_{cat}$ may also be influenced by the electrostatic/steric effects originating from the shielding of the single positive charge on the Mn(III) center. Thus the difference in the magnitude of lipophilicity between the metal-free ligands (formally +4) and the Mn(III) complexes (formally +5) becomes less noticeable as the alkyl chains get longer (Table 1). These $H_2P^{4+}$ compounds of formal +4 charge behave in solution kinetically as +1.6 to +1.8 electrolytes.[24] From methyl to n-butyl, log $k_{cat}$ decreases almost linearly (FIG. 4B, insert). Due to the exponential increase in $E_{1/2}$ along the series of Mn porphyrins (FIG. 3B, insert), the unfavorable electrostatic/steric effects are in part opposed and finally overcome by the progressively more favorable redox potentials that originate from increased desolvation (lipophilicity). Consequently, the very lipophilic n-octyl compound is essentially as potent an SOD mimic as the less lipophilic methyl and ethyl derivatives.

Regan et al[47] were able to uncouple the steric and solvation effects in reactions of chloride ions with methyl- and tert-butyl-substituted chloroacetonitrile, and showed that both were of comparable magnitudes. Similarly, the reactivity of N-alkylpyridylporphyrins are the result of the interplay of electronic, steric and salvation effects, the latter dominating with the more lipophilic members of the series.

Recent findings indicate that biologically relevant reactions, other than $O_2^-$ dismutation, can occur at the metal center in Mn porphyrins.[2,3,5,7,8,48-52] The same has been reported for the enzyme active site,[20,53-57] thus raising the complexity of the free radical chemistry and biology of the enzymes and their mimics. Reactive oxygen and nitrogen species are involved in direct damage of key biological targets such as nucleic acids, proteins and fatty acids, and there is an increasing amount of evidence that such species are also involved in the modulation of signaling processes.[14,58,59] Thus, it is important to understand the mechanisms of action of Mn porphyrins and related compounds. Based on the electrostatic, steric, solvation, and lipophilic effects observed in this study, we expect the members of N-alkylpyridyl series to differ one from another in in vivo models of oxidative stress injuries with respect to their specificity towards reactive oxygen and nitrogen species as well as with regard to their pharmacokinetics. Such work is in progress.

Abbreviations

SOD, superoxide dismutase; AN, acetonitrile; DMF, N,N'-dimethylformamide; NHE, normal hydrogen electrode; TLC, thin-layer chromatography; $H_2P^{4+}$, any meso tetrakis N-alkylpyridylporphyrin ligand; $Mn^{III/II}P^{4+/5+}$ any Mn(III/II) meso tetrakis N-alkylpyridylporphyrin; meso refers to the substituents at the 5,10,15, and 20 (meso carbon) position of the porphyrin core. $Mn^{III}T(alkyl)$-2(3,4)-$PyP^{5+}$, manganese(III) meso tetrakis(N-methyl, N-ethyl, N-n-propyl, N-n-butyl, N-n-hexyl, N-n-octyl)pyridinium-2(3,4)-yl)porphyrin; alkyl is M, methyl; E, ethyl; nPr, n-propyl; nBu, n-butyl; nHex, n-hexyl; nOct, n-octyl on the pyridyl ring; 2 is the ortho, 3, the meta and 4 the para isomer: $Mn^{III}TM\text{-}2\text{-}PyP^{5+}$ is AEOL-10112, and $Mn^{III}TE\text{-}2\text{-}PyP^{5+}$ is AEOL-10113; $Mn^{III}PTr(M\text{-}2\text{-}PyP^{4+}$, manganese(III) 5-phenyl-10,15,20-tris(N-methylpyridinium-2-yl)porphyrin; $Mn^{III}BM\text{-}2\text{-}PyP^{3+}$, manganese (III) meso bis(2-pyridyl)-bis(N-methylpyridinium-2-yl) porphyrin; $Mn^{III}TrM\text{-}2\text{-}PyP^{4+}$, 5-(2-pyridyl)-10,15,20-tris (N-methylpyridinium-2-yl)porphyrin; $Mn^{III}T(TMA)P^{5+}$, manganese(III) meso tetrakis(N, N, N-trimethylanilinium-4-yl)porphyrin; $Mn^{III}T(TFTMA)P^{5+}$, manganese(III) mesa tetrakis(2,3,5,6-tetrafluoro-N, N, N-trimethylanilinium-4-yl) poprhyrin; $Mn^{III}TCPP^{3-}$, manganese meso tetrakis(4-carboxylatophenyl)porphyrin; $MnTSPP^{3-}$, manganese(III) meso tetrakis(4-sulfonatophenyl)porphyrin; $Mn^{III}T(2,6\text{-}Cl_4\text{-}3\text{-}SO_3\text{-}P)P^{3-}$ manganese (III) meso tetrakis(2,6-dichloro-3-sulfonatophenyl)porphyrin; $Mn^{III}T(2,6\text{-}F_2\text{-}3\text{-}SO_3\text{-}P)P^{3-}$, manganese (III) meso tetrakis(2,6-difluoro-3-sulfonatophenyl)porphyrin; $Mn^{III}T(2,4,6\text{-}Me_3\text{-}3\text{-}(SO_3)_4\text{-}P)P^{7-}$, manganese(III) 5,10,15,20-tetrakis(2,4,6,-trimethyl-3,5-disulfonatophenyl)porphyrin; $Mn^{III}hematoP^-$, manganese(III) hematoporphyrin IX.

REFERENCES

1. R. F. Pasternack, A. Banth, J. M. Pasternack and C. S. Johnson, *J. Inorg. Biochem.* 1981, 15, 261 (b) R. F. Pasternack and B. J. Halliwell, *J. Am. Chem. Soc.* 1979,101, 1026.
2. I. Batinić-Haberle, *Methods Enzymol.* 2002, 349, 223.
3. I. Spasojević and I. Batinić-Haberle, *Inorg. Chim. Acta*, 2001, 317, 230.
4. I. Batinić-Haberle, I. Spasojević, P. Hambright, L. Benov, A. L. Crumbliss and I. Fridovich, *Inorg. Chem.* 1999, 38, 4011.
5. G. Ferrer-Sueta, I. Batinić-Haberle, I. Spasojević, I. Fridovich and R. Radi, *Chem. Res. Toxicol.* 1999, 12, 42.
6. R. Kachadourian, I. Batinić-Haberle and I. Fridovich, *Inorg. Chem.* 1999, 38, 391.
7. J. Lee, J. A. Hunt and J. T. Groves, *J. Am. Chem. Soc.* 1998, 120, 6053.
8. J. P. Crow, *Arch. Biochem. Biophys.* 1999, 371, 41.
9. M. Patel and B. J. Day, *Trends Pharmacol.* 1999, 20, 359.
10. (a) K. Aston, N. Rath, A. Naik, U. Slomczynska, O. F. Schall and D. P. Riley, *Inorg. Chem.* 2001, 40, 1779. (b) S. Cuzzocrea, E. Mazzon, L. Dugo, A. P. Caputi, K. Aston, D. P. Riley and D. Salvemini, *Br. J. Pharmacol.* 2001, 132, 19.
11. (a) S. Melov, J. Ravenscroft, S. Malik, M. S. Gill, D. W. Walker, P. E. Clayton, D. C. Wallace, B. Malfroy, S. R. Doctrow and G. J. Lithgow, *Science,* 2000, 289, 1567. (b) K. Baker, C. Bucay Marcus, K. Huffman, H. Kruk, B. Malfroy and S. R. Doctrow, *J. Pharmacol. Exp. Ther.,* 1998, 284, 215.
12. I. Batinić-Haberle, L. Benov, I. Spasojević and I. Fridovich, *J. Biol ChewM*, 1998, 273, 24521.
13. I. Spasojević, R. Menzeleev, P. S. White and I. Fridovich, *Inorg. Chem.,* 2002, submitted.
14. G. B. Mackensen, M. Patel, H. Sheng, C. C. Calvi, L Batinić-Haberle, B. J. Day, L. P. Liang, I. Fridovich, J. D. Crapo, R. D. Pearlstein and D. S. Warner, *J. Neurosci.,* 2001, 21, 4582.
15. J. D. Piganelli, S. C. Flores, C. Cruz, J. Koepp, I. Batinić-Haberie J. Crapo, B. J. Day, R. Kachadourian, R. Young, B. Bradley and K. Haskins, *Diabetes,* 2002, 51, 347.
16. M. Aslan, T. M. Ryan, B. Adler, T. M. Townes, D. A. Parks, J. A. Thompson, A. Tousson, M. T. Gladwin, M. M. Tarpey, M., R. P. Patel, I. Batinić-Haberle, C. R. White and B. A. Freeman, *Proc. Natl. Acad Sci. USA,* 2001, 98, 15215.
17. (a) I. Batinić-Haberle, I. Spasojević, I. Fridovich, M. S. Anscher and Z. Vujaskovic, Proc of the 43$^{rd}$ Annual Meeting of American Society for Therapeutics in Radiation Onciology, San Francisco 2001, 235-236. (b) Z. Vuja šković, I. Batinić-Haberle, I. Spasojević, T. V. Samulski, M. W. Dewhirst and M. S. Anscher, Annual Meeting of Radiation Research Society, San Juan, Puerto Rico 2001. (c) Z. Vujašković, I. Batinić-Haberle, I. Spasojević, Irwin Fridovich, M. S. Anscher and M. W. Dewhirst, *Free Rad. Biol. Med.* 2001, S128.
18. W. R. Waud, F. O. Brady, R. D. Wiley and K. V. Rajagopalan, *Arch. Biochem. Biophys.* 1975, 19, 695.
19. T. Kaufmann, T., B. Shamsai, R. S. Lu, R. Bau and G. M. Miskelly, *Inorg. Chem.* 1995, 34, 5073.
20. I. M. Kolthof and W. J. Tomsicek, W. J., *J. Phys. Chem.* 1935, 39, 945.
21. L Batinić-Haberle, I. Spasojević, R. D. Stevens, P. Hambright, A. N. Thorpe, J. Grodkowski, P. Neta and I. Fridovich, *Inorg. Chem.* 2001, 40, 726.
22. J. M. McCord and I. Fridovich, *J. Biol. Chem.* 1969, 244, 6049.
23. I. Batinić-Haberle, S. I. Liochev, I. Spasojević and I. Fridovich, *Arch. Biochem. Biophys.* 1997, 343, 225.
24. P. Hambright, I. Spasojević, I. Fridovich and I. Batinić-Haberle, in preparation.
25. P. Hambright, *Water-Soluble Metalloporphyrins* in The Porphyrin Handbook, K. M. Kadish, K. M. Smith, R. Guillard, Eds. Academic Press, N.Y. 2000, Chapter 18.
26. T. P. G. Sutter and P. Hambright, *J. Coord. Chem.* 1993, 30, 317.
27. L. R. Robinson and P. Hambright, *Inorg. Chem.,* 1992, 31, 652.
28. J. B. Reid and P. Hambright, *Inorg. Chem.* 1977, 16, 968.
29. M. Inamo, N. Kamiya, Y. Inada, M. Nomura and S. Funahashi, *Inorg. Chem.,* 2001, 40, 5636.
30. P. B. Chock and P. Hambright, *J. Am. Chem. Soc.* 1974, 96, 3123.
31. S. Funahashi, Y. Inada and M. Inamo, *Anal. Sci.* 2001, 17, 917.
32. T. P. G. Sutter, R. Rahimi, P. Hambright, J. Bommer, M. Kumar and P. Neta, *J. Chem. Soc. Faraday Trans.* 1993, 84, 495.
33. B. Cheng, O. Q. Munro, H. M. Marques and W. R. Scheidt, *J. Am. Chem. Soc.* 1997,119, 10732.
34. R. F. Pasternack, N. Sutin and D. H. Turner, *J. Am. Chem. Soc.* 1976, 98, 1908.
35. P. Hambright, T. Gore and K. Burton, *Inorg. Chem.* 1976, 15, 2314.
36. J. Davila, A. Harriman, M. -G. Richoux and L. R. Milgrom, *J. Chem. Soc. Chem. Commun.* 1987, 525.
37. I. Batinić-Haberle, R. D. Stevens and I. Fridovich, *J. Porphyrins Phthalocyanines,* 2000, 4, 217.
38. R. Kachadourian, N. Srinivasan, C. A. Haney and R. D. Stevens, *J. Porphyrins Phthalocyanines,* 2001, 5, 507.
39. Vance, C. K and Miller, A. -F., *Biochemistry,* 2001, 40, 13079.
40. (a) G. D. Lawrence and D. T. Sawyer, *Biochemistry,* 1979, 18, 3045. (b) W. C. Jr. Barrette, D. T. Sawyer, J. A. Free and K. Asada, *Biochemistry* 1983, 22, 624.
41. Wood, P. M., *Biochem. J.,* 1988, 253, 287.
42. Vance, C. K. and Miller, A.-F., *J. Am. Chem Soc.,* 1998, 120, 461.
43. R. M. Ellerby, D. E. Cabelli, J. A. Graden and J. S. Valentine, *J. Am. Chem. Soc.,* 1996, 118, 6556.

44. D. Klug-Roth, I. Fridovich and J. Rabani, *J. Am. Chem. Soc.*, 1973, 95, 2786.
45. R. A. Marcus, *Annu. Rev. Phys. Chem.*, 1964, 15, 155.
46. *CRC Handbook of Chemistry and Physics*, D. R. Lide, Editor-in-Chief, 74th Edition, 1993-1994, CRC Press, Boca Raton.
47. I. Spasojević, I. Batinić-Haberle and I. Fridovich, *Nitric Oxide: Biology and Chemistry* 2000, 4, 526.
48. (a) C. K. Regan, S. L. Craig and J. I. Brauman, *Science*, 2002, 295, 2245.
49. R. Shimanovich and J. T. Groves, *Arch. Biochem. Biophys.*, 2001, 387, 307.
50. N. Jin, J. L. Bourassa, S. C. Tizio and J. T. Groves, *Angew. Chem. Int. Ed.*, 2000, 39, 3849.
51. H. Zhang, J. Joseph, M. Gurney, D. Becker and B. Kalyanaraman, *J. Biol. Chem.*, 2002, 277, 1013.
52. N. Motohashi and Y. Saito, *Chem. Pharm. Bull.*, 1995, 43, 505.
53. C. Quijano, D. Hernandez-Saavedra, L. Castro, J. M. McCord, B. A. Freeman and R. Radi, *J. Biol. Chem.*, 2001, 276, 11631.
54. (a) S. L. Jewer, A. M. Rocklin, M. Ghanevati, J. M. Abel and J. A. Marach, *Free Rad. Biol. Med.*, 1999, 26, 905. (b) S. P. A. Goss, R. J. Singh and B. Kalyanaraman, *J. Biol. Chem.*, 1999, 274, 28233. (c) S. I Liochev and I. Fridovich, *Free Rad. Biol. Med.*, 199, 27, 1444.
55. (a) A. G. Estevez, J. P. Crow, J. B. Sampson, L Reither, J. Zhuang, G. J. Richardson, M. M. Tarpey, L. Barbeito and J. S. Beckman, *Science*, 1999, 286, 2498. (b) S. I. Liochev and I. Fridovich, *J. Biol. Chem.*, 2001, 276, 35253.
56. S. I. Liochev and I. Fridovich *J. Biol. Chem.*, 2000, 275, 38482.
57. E. D. Coulter, J. P. Emerson, D. M. Jr., Kurtz and D. E. Cabelli, *J. Am. Chem. Soc.*, 2000, 122, 11555.
58. B. M. Matata and M. Galinanes, *J. Biol. Chem.*, 2002, 277, 2330.
59. (a) Z. Vujašković, I. Batinić-Haberle, M. S. Anscher, Z. N. Rabbani, T. V. Samulski, K. Amin, M. W. Dewhirst and Z. Haroon, Proc. of the 43rd Annual Meeting of American Society for Therapeutics in Radiation Onciology, San Francisco 2001, 88-89. (b) Z. Vujašković, I. Batinić-Haberle, Z. N. Rabbani, Q.-F. Feng, S. K Kang, L Spasojević, T. V. Samulski, I. Fridovich, M. W. Dewhirst, M. S. Anscher, *Free Rad. Biol. Med.* In press.

TABLE 1

Metal-Centered Redox Potentials $E_{1/2}$, log $k_{cat}$ for $O_2$ Dismutation, and Chromatographic $R_f$ values.

| Porphyrin | $R_f$[a] | $pK_{a2}$[b] | $E_{1/2}$[c] mV vs NHE | log $k_{cat}$[d] |
|---|---|---|---|---|
| $Mn^{III}TM$-2-$PyP^{5+}$ | 0.09 (0.13) | 10.9 | +220 | 7.79 |
| $Mn^{III}TE$-2-$PyP^{5+}$ | 0.13 (0.21) | 10.9 | +228 | 7.76 |
| $Mn^{III}TnPr$-2-$PyP^{5+}$ | 0.20 (0.31) | 11.4 | +238 | 7.38 |
| $Mn^{III}TnBut$-2-$PyP^{5+}$ | 0.33 (0.46) | 11.7 | +254 | 7.25 |
| $Mn^{III}TnHex$-2-$PyP^{5+}$ | 0.57 (0.63) | 12.2 | +314 | 7.48 |
| $Mn^{III}TnOct$-2-$PyP^{5+}$ | 0.80 (0.86) | 13.2 | +367 | 7.71 |

[a] $R_f$ (compound path/solvent path) on silica gel TLC plates in 1:1:8 $KNO_3$-saturated $H_2O$:$H_2O$:acetonitrile. $R_f$ for the metal-free porphyrins are in parentheses.
[b] $pK_{a2}$ determined at 25° C. ionic strength 0.10 ($NaNO_3$/NaOH).
[c] $E_{1/2}$ determined in 0.05 M phosphate buffer (pH 7.8, 0.1 M NaCl).
[d] $K_{cat}$ determined using the cytochrome c assay. in 0.05 M phosphate buffer, pH 7.8, at (25 ± 1) °C.

TABLE 2

Molar Absorptivities of Tetrakis (N-alkylpyridinium-2-yl)porphyrin chlorides and their Mn(III) Complexes.

| Porphyrin | $\lambda_{nm}$(log ϵ)[a] |
|---|---|
| $H_2TM$-2-$PyP^{4+}$ | 413.2(5.32); 510.4(4.13); 544.4(3.49); 581.4(3.72); 634.6(3.13) |
| $H_2TE$-2-$PyP^{4+}$ | 414(5.33); 511(4.20); 545(3.58); 582(3.80); 635(3.38); |
| $H_2TnPr$-2-$PyP^{4+}$ | 415(5.38); 511.5(4.24); 545(3.62); 583(3.84); 635(3.37) |
| $H_2TnBut$-2-$PyP^{4+}$ | 415(5.37); 511(4.24); 544(3.60); 583(3.84); 636(3.39) |
| $H_2TnHex$-2-$PyP^{4+}$ | 415.5(5.34); 510.5(4.24); 543(3.62); 584.5(3.84); 638(3.43) |
| $H_2TnOct$-2-$PyP^{4+}$ | 416.5(5.31); 510(4.25); 542(3.59); 585(3.82); 639.5(3.43) |
| $Mn^{III}TM$-2-$PyP^{5+}$ | 363.5(4.64); 411(4.27); 453.4(5.11); 499(3.66); 556(4.03); 782(3.15) |
| $Mn^{III}TE$-2-$PyP^{5+}$ | 363.5(4.68); 409(4.32); 454(5.14); 499(3.75); 558(4.08); 782(3.26) |
| $Mn^{III}TnPr$-2-$PyP^{5+}$ | 363(4.70); 411(4.37); 454(5.21); 498(3.81); 559(4.12); 782(3.35) |
| $Mn^{III}TnBut$-2-$PyP^{5+}$ | 364(4.70); 410(4.35); 454(5.23); 498(3.83); 559(4.14); 781(3.33) |
| $Mn^{III}TnHex$-2-$PyP^{5+}$ | 364.5(4.70); 415(4.57); 454.5(5.21); 507(3.85); 560(4.12); 780(3.30) |
| $Mn^{III}TnOct$-2-$PyP^{5+}$ | 364(4.72); 414(4.44); 454.5(5.24); 500.5(3.84); 559.5(4.14); 781(3.25) |

[a] The molar absorptivities were determined in water at room temperature.

TABLE 3

Electrospray Mass Spectrometry Results for $H_2T(alkyl)$-2-$PyP^{4+}$ Compounds.[a]

| | m/z | | | | | |
|---|---|---|---|---|---|---|
| Species[b] | M | E | nPr | nBu | nHex | nOct |
| $H_2P^{4+}$/4 | 169 | 184 | 198 | 212 | 239 | 268 |
| $H_2P^{4+}$ + AN/4 | 180 | 194 | 208 | 222 | 250 | |
| $H_2P^{4+}$ + 2AN/4 | 190 | | | | | |
| $H_2P^{4+}$ − $H^+$/3 | 226 | 245 | 263 | 282 | 319 | 357 |
| $H_2P^{4+}$ − $H^+$ + AN/3 | 240 | 258 | 278 | | | |
| $H_2P^{4+}$ − $H^+$ + $H_2O$/3 | | | | 288 | | |
| $H_2P^{4+}$ − $H^+$ + $Cl^-$/2 | | | | | 496 | |
| $H_2P^{4+}$ − $a^+$/3 | | 235 | 249 | 263 | 291 | 319 |
| $H_2P^{4+}$ − $a^+$ − $H^+$/2 | | 352 | 374 | 394 | 436 | |
| $H_2P^{4+}$ − $a^+$ + $H_2O$/3 | | 255 | | | | |
| $H_2P^{4+}$ − $2a^+$/2 | | | 352 | 366 | | |
| $H_2P^{4+}$ + $H^+$/5 | 136 | | | | | |
| $H_2P^{4+}$ + $H^+$ + AN/5 | 143 | | | | | |
| $H_2P^{4+}$ + $H^+$ + 2AN/5 | 152 | | | | | |
| $H_2P^{4+}$ + $H^+$ + $2Cl^-$/3 | | | | | 343 | 381 |
| $H_2P^{4+}$ + $2H^+$ + $2Cl^-$/4 | | | | | | 286 |
| $H_2P^{4+}$ − $2H^+$/2 | 339 | 367 | 395 | 423 | 479 | |

[a] 0.5 mM solutions of $H_2P^{4+}$ in 1:1 acetonitrile:water, 20 V cone voltage.
[b] AN denotes acetonitrile and a is an alkyl group.

TABLE 4

Electrospray Mass Spectrometry for $Mn^{III}T(alkyl)$-2-$PyP^{5+}$ Porphyrins.[a]

| | m/z | | | | | |
|---|---|---|---|---|---|---|
| Species[b] | M | E | nPr | nBu | nHex | nOct |
| $Mn^{III}P^{5+}$/5 | 146 | 157 | | | | |
| $Mn^{III}P^{5+}$ + AN/4 | 155 | 166 | 177 | 188 | | |
| $Mn^{III}P^{5+}$ + 2AN/5 | 163 | 174 | 185 | 196 | | |
| $Mn^{III}P^{5+}$ + 3AN/5 | 171 | 182 | 193 | 205 | | |
| $Mn^{III}P^{5+}$ + 4AN/5 | 179 | 190 | | 213 | | |
| $Mn^{III}P^{5+}$ + 5AN/5 | 187 | 198 | | | | |

TABLE 4-continued

Electrospray Mass Spectrometry for $Mn^{III}T(alkyl)$-2-$PyP^{5+}$ Porphyrins.[a]

| Species[b] | M | E | nPr | nBu | nHex | nOct |
|---|---|---|---|---|---|---|
| $Mn^{III}P^{5+}$ + 6AN/5 | 195 | | | | | |
| $Mn^{III}P^{5+}$ + $H_2O$/5 | 150 | | | | | |
| $Mn^{III}P^{5+}$ + $Cl^-$/4 | 192 | 206 | | 234 | 262 | 290 |
| $Mn^{III}P^{5+}$ + $2Cl^-$/3 | 267 | 286 | 305 | 323 | 361 | 398 |
| $Mn^{III}P^{5+}$ + $Cl^-$ + AN/4 | 202 | 216 | 230 | 244 | 272 | |
| $Mn^{III}P^{5+}$ − a/4 | | | 200 | | | |
| $Mn^{III}P^{5+}$ − a + AN/4 | | 200 | | 221 | 242 | |
| $Mn^{III}P^{5+}$ − a + $Cl^-$/3 | | 264 | 279 | 293 | 321 | 349 |
| $Mn^{III}P^{5+}$ − 2a/3 | | 243 | 252 | 262 | | 299 |
| $Mn^{III}P^{5+}$ − 2a + AN/3 | | | | 275 | 294 | |
| $Mn^{II}P^{4+}$/4 | 183 | 197 | 211 | | | 281 |
| $Mn^{II}P^{4+}$ + AN/4 | 193 | 207 | 221 | 235 | 263 | |
| $Mn^{II}P^{4+}$ + 2AN/4 | 204 | | | | | |
| $Mn^{II}P^{4+}$ + $Cl^-$/3 | 255 | 274 | 293 | 312 | 349 | 387 |
| $Mn^{II}P^{4+}$ − a/3 | | 253 | 266 | 281 | 309 | 337 |
| $Mn^{III}P^{5+}$ − $Mn^{3+}$ + $H^+$/3 | | | | 281 | 319 | 357 |
| $M^{II}P^{-3+}$/3 or $Mn^{I}P^{3+}$/3 | | | | 294 | 337 | 375 |

[a] 0.5 mM solutions of $Mn^{III}P^{5+}$ in 1:1 acetonitrile:water, 20 V cone voltage.
[b] AN denotes acetonitrile and a is an alkyl group.

What is claimed is:

1. A compound of formula

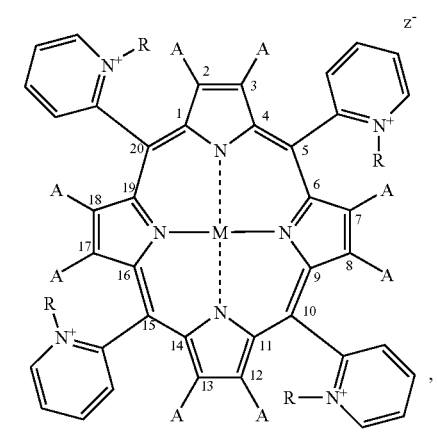

I

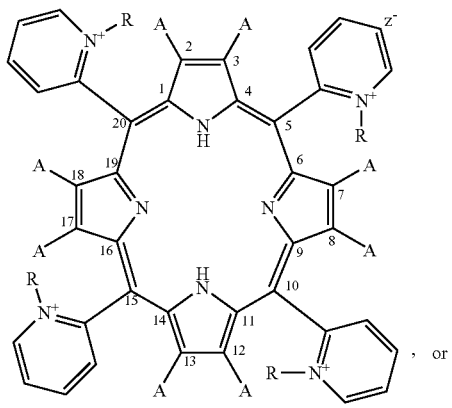

III

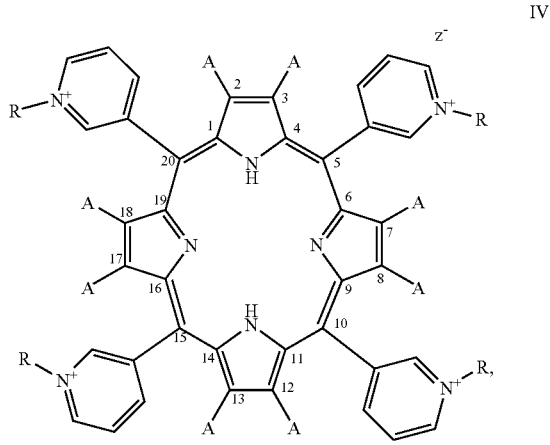

IV wherein
each R is, independently, an alkyl group of greater than 8 carbons,
each A is, independently, hydrogen or a halogen,
M is a metal selected from the group consisting of manganese, iron, copper, cobalt, nickel and zinc, and
$Z^-$ is a counterion.

2. The compound according to claim 1 wherein at least one A is a halogen.

3. The compound according to claim 1 wherein said compound is of Formula I or III.

4. The compound according to claim 3 wherein said compound is of Formula I and M is manganese.

5. A compound of formula

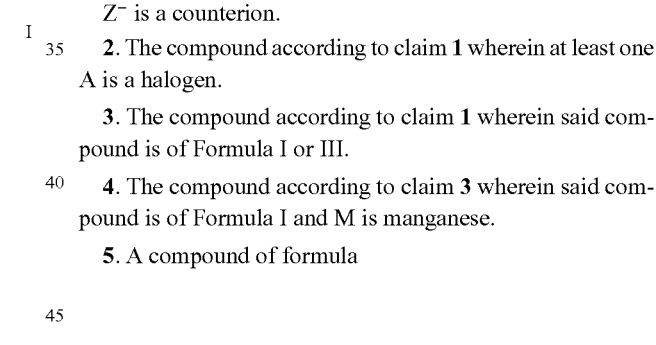

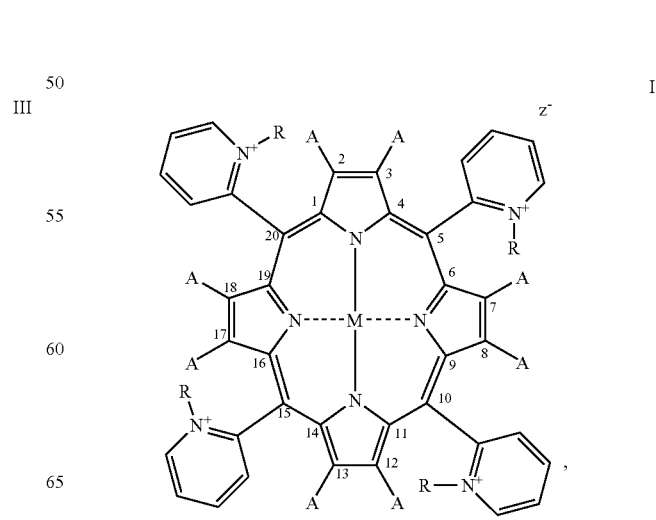

I

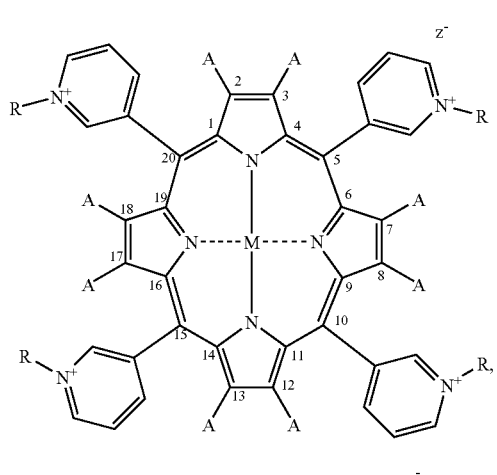

II

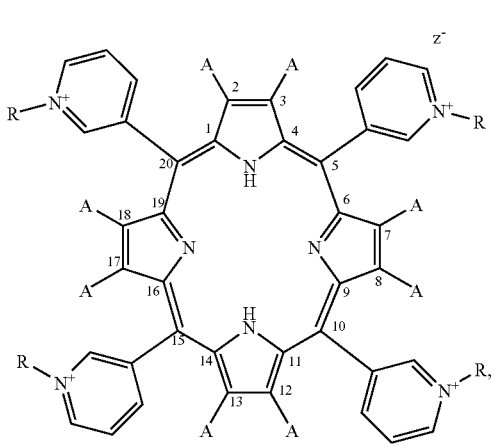

IV

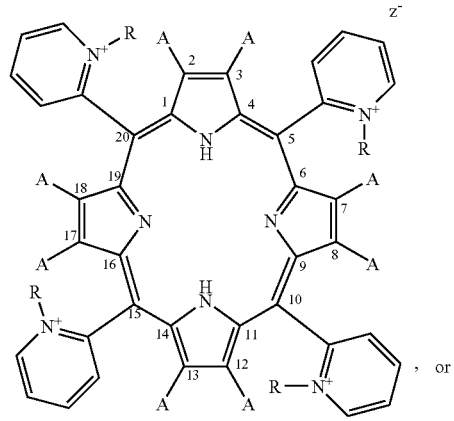

III wherein
each R is, independently, an alkyl group of greater than 8 carbons, each A is, independently, hydrogen or a halogen, M is a metal selected from the group consisting of manganese, iron, copper, cobalt, and nickel, and $Z^-$ is a counterion;

with the proviso that when said compound is of Formula II, each R is, independently, an $C_9$-$C_{12}$ alkyl group.

6. The compound according to claim 5 wherein at least one A is a halogen.

* * * * *